| United States Patent [19] | [11] Patent Number: 4,617,298 |
| Bodor et al. | [45] Date of Patent: Oct. 14, 1986 |

[54] METHOD AND COMPOSITIONS FOR WEIGHT CONTROL

[75] Inventors: Nicholas S. Bodor; Kerry S. Estes; James W. Simpkins, all of Gainesville, Fla.

[73] Assignee: University of Florida, Gainesville, Fla.

[21] Appl. No.: 790,159

[22] Filed: Oct. 22, 1985

[51] Int. Cl.$^4$ ............................................. A61K 31/58
[52] U.S. Cl. ..................................... 514/176; 514/909
[58] Field of Search ................................ 514/176, 909

[56] References Cited

U.S. PATENT DOCUMENTS

| 4,035,507 | 7/1977 | Bodor et al. | 424/319 |
| 4,065,566 | 12/1977 | Bodor et al. | 424/266 |
| 4,202,323 | 5/1980 | Zweig et al. | 424/1 |
| 4,206,220 | 6/1980 | Sloan | 424/274 |
| 4,242,330 | 12/1980 | Hussain et al. | 424/235 |
| 4,479,932 | 10/1984 | Bodor | 424/9 |

OTHER PUBLICATIONS

The Friday Evening Post, Aug. 14, 1981–Health Center Commun., Univ. of Fla.–Gainesville, Fla.
Chem. & Engineering News, Dec. 21, 1981, pp. 24–25.
Science News, Jan. 2, 1982, vol. 121, #1, p. 7.
Brewster, III–Dis. Abst. Int. B. vol. 43(9), p. 2910B.
Bodor et al.–Science 190 (1975), pp. 155–156.
Bodor et al.–Science 214 (1981) pp. 1370–1371.
Bodor et al.–J. Pharm. Sci. 67 (1978)–pp. 685–687.
Shek et al.–J. Med. Chem. 19 (1976), pp. 113–117.

*Primary Examiner*—Douglas W. Robinson
*Attorney, Agent, or Firm*—Mary Katherine Baumeister; Dennis P. Clarke

[57] ABSTRACT

The invention provides a method for controlling mammalian body weight using a compound of the formula

[E—DHC]     (I)

or a non-toxic pharmaceutically acceptable salt thereof, wherein [E] is an estrogen and [DHC] is the reduced, biooxidizable, blood-brain barrier penetrating, lipoidal form of a dihydropyridine⇌pyridinium salt redox carrier. Novel compositions for weight control comprising a compound of formula (I) or its salt are also disclosed. A preferred compound for use in the subject method and compositions is an estradiol derivative, namely, 17 β-[(1-methyl-1,4-dihydro-3-pyridinyl)carbonyloxy]estra-1,3,5(10)-trien-3-ol.

27 Claims, 4 Drawing Figures

METHOD AND COMPOSITIONS FOR WEIGHT CONTROL

FIELD OF THE INVENTION

The present invention relates to the use of brain-specific dihydropyridine redox carrier type derivatives of estrogenic agents for mammalian weight control. The invention further relates to compositions containing such carrier-linked estrogens which are useful for weight control in mammals.

BACKGROUND OF THE INVENTION

Overweight is considered a very important problem in today's society, not only because of cosmetic considerations but also for medical reasons, especially when weight exceeds normal ranges to the point of obesity. Typically, dieting to reduce food intake, along with increased exercise, is used to reduce weight (or to prevent weight gain). Persistent and strict dieting is very difficult to maintain, however, and a number of drugs have been used in the past in attempts to suppress appetite and, consequently, food intake, and thus to make adherence to a dietary regime more tolerable. Amphetamine-type drugs have been used for this purpose for some time, but these drugs have dangerous side effects, present a significant addiction problem, are not always effective and are subject to tolerance development within a short period of time. More recently, naltrexone and other narcotic antagonists have been proposed for use as appetite suppressants. Nevertheless, there remains a serious need for yet other pharmacological means for weight control.

It is now well recognized that food intake and body weight vary during the estrous cycle in the rat. A consistent observation is that food intake and body weight decrease during the follicular phase of the estrous cycle when serum concentration of estradiol increases. In contrast, food intake and body weight increase during the luteal phase of the rat's estrous cycle when estradiol levels decrease and progesterone concentrations are elevated. Similarly, food intake and body weight increase after ovariectomy, a state of gonadal steroid deprivation, and during pregnancy and pseudopregnancy, when progesterone levels are increased. These observations indicate that endogenous estradiol is suppressory to food intake and the lack of estradiol is associated with enhanced food intake and body weight gain. It also would appear that the effects of estradiol on food intake are more transistory than the effects on body weight; thus, the actions of estrogen may be much more complex than simple appetite suppression. For representative literature in this area, see Tarttelin et al, *Acta Endocr.* 72: 551-568 (1973); Yoshinaga et al, *Endocrinol.* 85: 103-112 (1969); Landau et al, *Horm. Behav.* 7: 29-39 (1976); Wade and Zucker, *J. Comp. Physiol. Psychol.* 72: 328-336 (1970); Wade, *Physiol Behav.* 8: 523-534 (1972). It is interesting to note that while Tarttelin et al report potent effects of estradiol administration in ovariectomized rats, they note that estrogen treatment of intact females interrupted normal vaginal cycles but did not significantly affect food intake or body weight. Hervey et al, in *J. Endocrinol.* 33: 9-10 (1965), similarly noted loss of weight following estradiol administration to castrated rats of either sex, but little effect on the body weight of intact females similarly dosed with estradiol.

In ovariectomized rats, administration of estradiol, but not of progesterone or of testosterone, suppresses food intake and reduces body weight. Two lines of evidence indicate that the effects of estradiol on body weight are mediated by the central nervous system (CNS). First, the effects of administration of estradiol on reducing food intake and body weight occur in rats even after ovariectomy and hypophysectomy (removal of the pituitary gland) or adrenalectomy; Wade, *Physiol. Behav.* 8: 523-534 (1972). Secondly, implantation of crystalline estradiol benzoate into various hypothalamic regions reduced food intake in rats; Wade and Zucker, *J. Comp. Physiol. Psychol.* 72: 328-336 (1970). In that study, progesterone was found to be considerably less effective than estradiol, and testosterone was found to be ineffective. The effectiveness of hypothalamic implants of estradiol in suppressing food intake is not surprising since this brain region regulates food and water intake and neurons which concentrate this gonadal steroid have been described.

Nevertheless, the effects of estradiol on food intake (FI), water intake (WI) and a body weight (BWt) may be indicative of more complex effects not necessarily dependent on the CNS. As Tarttelin et al, in *Acta Endocr.* 72: 551-568 (1973), observe: "The initial effect on FI must be by action somewhere in the central nervous system but the long-term BWt and WI effects indicate that oestrogen might have some profound effect on body metabolism which need not be dependent on direct CNS participation, but rather may depend on other hormones with a peripheral action such as thyroid hormones, growth hormones or adrenal corticosteroids, although oestrogen could affect secretion of these hormones at the hypothalamic level."

The cyclic variation in food intake and body weight has been described for other species as well. The hamster, guinea pig, ewe, pigtailed monkey, baboon, rhesus monkey and human female show reduced food intake and body weight during the follicular (increasing estrogen) phase of their ovarian cycles and increase in these during the luteal (high progesterone/low estrogen activity) phase of their ovarian cycles. Additionally, systemic administration of estradiol to ovariectomized rhesus monkeys depresses food intake, while progesterone is ineffective. Thus, the suppressory effect of estradiol on food intake appears to be common to many mammalian species. See, for example, Morin et al, *J. Comp. Physiol. Psychol.* 92: 1-6 (1978); Czaja, *Physiol. Behav.* 14: 579-587 (1975); Rosenblatt et al, *Physiol. Behav.* 24: 447-449 (1980); Dalvit, *Am. J. Clin. Nutr.* 34: 1811-1815 (1981); Czaja et al, *Hormone Behav.* 6: 329-349 (1975); and Gilbert et al, *S. Afr. J. Med. Sci.* 21: 75-88 (1956).

There have been relatively few studies on steroid modulation of food intake and body weight in humans. Morten et al, in *Am. j. Obstet. Gynecol.* 65: 1182-1191 (1953), reported on a study of the premenstrual syndrome (PMS) in prison inmates. PMS is a late luteal phase condition. Among the women studied, 37% reported a craving for sweets and 23% indicated an increase in appetite associated with this state. Similarly, a craving for sweets was a frequently reported PMS phenomenon in 45 women studied by Fortin et al, as noted by Smith et al. *Psychosom. Med.* 31: 281-287 (1969). In Smith et al's own study, a craving for sweets and compulsive eating were associated with "a more frequent depression" during the late luteal phase of the menstrual cycle.

In a more quantitative analysis of the role of the gonadal steroids in body weight regulation in human subjects, Dalvit, *Am. J. Clin. Nutr.* 34: 1811–1815 (1981), recently reported that the calorie intake of 8 women was significantly higher during the luteal (high progesterone) phase than during the follicular (increasing estrogen) phase of two consecutive menstrual cycles. Pliner et al studied 34 women and observed, in *Physiol. Behav.* 30: 663–666 (1983), that the decrease in food intake during the follicular phase was associated with weight loss and that the increase in food intake during the luteal phase was concurrent with weight gain. Thus, in women, endogenously released estradiol has a consistent, albeit subtle, suppressory effect on food intake and body weight.

The use of oral contraceptives, which contain progestins and semi-synthetic estrogens, has been variously reported to cause increase or decrease in weight; these effects have been neither confirmed nor refuted. Fluid retention has been noted in "pill" users and this may be associated with the reports of weight gain in women who use oral contraceptives. Thus, there is no consistent evidence for the effects of oral contraceptives on body weight in women.

At the present time, estrogens are generally administered to control symptoms of menopause; for postmenopausal osteoporosis, dysmenorrhea, menorrhagia, amenorrhea, atrophic vaginitis, ovarian dwarfism and post partum breast engorgement; in combination with progestins in oral contraceptives; in breast cancer; and in men in prostatic carcinoma. These uses are a reflection of the significant physiological and pharmacological actions of the estrogens, especially on the reproductive organs. Unfortunately, some significant toxic effects, including increased risk of thromboembolism, thrombophlebitis and endometrial carcinoma, are associated with the use of these hormones in therapy.

Recently, a chemical delivery system (CDS) has been devised which promises to deliver centrally acting drugs, such as the estrogens, to the brain in a sustained and site-specific manner. In accord with this system, the desired centrally-mediated hormonal effects of the estrogens can be achieved without the high concentrations throughout the body which are believed to be responsible for the significant toxic effects generally associated with use of these drugs. The estrogen-chemical delivery system is generally described in Bodor U.S. Pat. No. 4,479,932 issued to U. OF FLORIDA on Oct. 30, 1984, and more specifically in U. OF FLORIDA'S International Application No. PCT/US83/00725 (published under International Publication No. WO83/03968), in Bodor U.S. Pat. No. 4,540,564 issued to U. OF FLORIDA on Sept. 10, 1985. Briefly, according to the estrogen-CDS system, the target estrogen is tethered to a reduced, blood-brain barrier penetrating lipoidal form of a dihydropyridine$\rightleftharpoons$pyridinium salt type redox carrier. Oxidation of the dihydropyridine carrier moiety in vivo to the ionic pyridinium salt type estrogen/carrier entity prevents elimination thereof from the brain, while elimination from the general circulation is accelerated, and subsequent cleavage of the quaternary carrier/estrogen species results in sustained delivery of the estrogen in the brain and facile elimination of the carrier moiety. As stated in the aforementioned U.S. Pat. No. 4,479,932, the rationale for brain delivery of the steroid hormones, e.g. estradiol, at least in part derives from the fact that recent studies of histological mapping of hormone-sensitive and specific steroid binding cells in the brain have underscored the importance of steroid action in the brain on sexual behavior. Further details of the estrogen-chemical delivery system are given hereinbelow.

SUMMARY AND OBJECTS OF THE INVENTION

One object of the present invention is to provide a new method for achieving weight control in mammals, particularly in humans and in domestic animals such as dogs and cats.

Another object of the present invention is to provide novel compositions for use in mammalian weight control.

Yet another object of this invention is to provide a new use for brain-specific dihydropyridine redox carrier type derivatives of estrogenic agents in controlling body weight in mammals.

Still another object of this invention is to provide novel long-acting compositions containing brain-specific dihydropyridine redox carrier type derivatives of estrogenic agents for use as mammalian weight control agents.

Another object of the present invention is to provide novel means for treating and/or preventing obesity.

Yet another object of the invention is to use a selected group of estrogen derivatives to elicit inhibitory effects on appetite, food consumption and/or body weight in mammals, especially in normal adult mammals, preferably without producing pronounced estrogenic effects on the reproductive system.

In accord with the foregoing objects of the invention, there is described herein a novel method for controlling body weight, said method comprising administering to a mammal in need of such treatment, an effective weight-controlling amount of a compound of the formula $$[\text{E-DHC}] \tag{I}$$

or a non-toxic pharmaceutically acceptable salt thereof, wherein [E] is an estrogen and [DHC] is the reduced, biooxidizable, blood-brain barrier penetrating lipoidal form of a dihydropyridine$\rightleftharpoons$pyridinium salt redox carrier. Preferably, the selected compound of formula (I) is administered in the form of a novel composition comprising an amount of said compound sufficient to effect weight control but insufficient to cause pronounced peripheral estrogenic effects in the mammalian species to which the compound is administered (e.g. total inhibition of ovulation and/or cessation of estrous or menstrual cycles).

BRIEF DESCRIPTION OF THE DRAWINGS

Other objects and advantages of the present invention will be apparent from the following detailed description and accompanying drawings, in which.

DETAILED DESCRIPTION OF THE INVENTION

Figure 1:
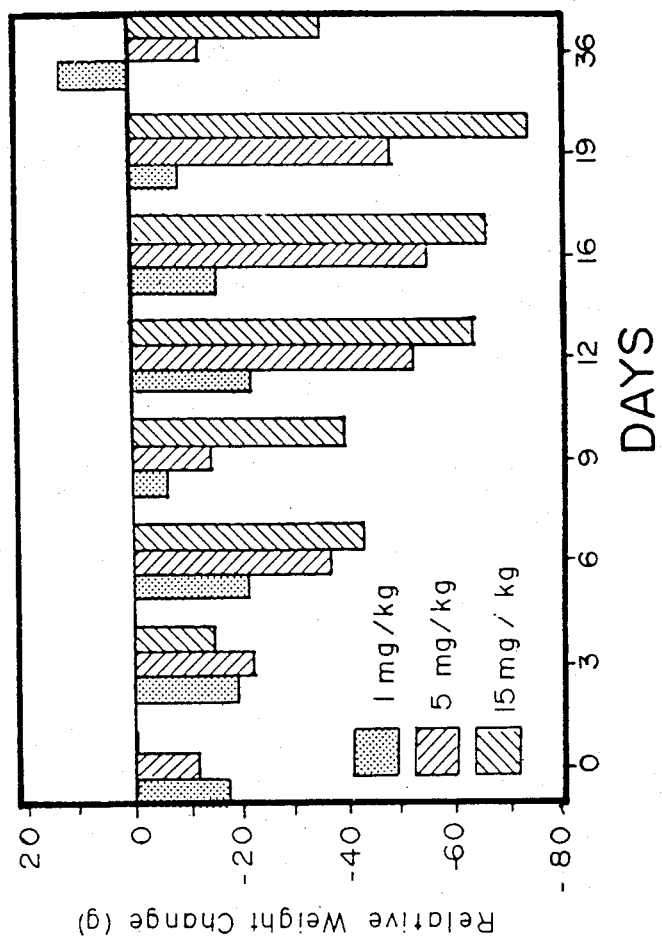
FIG. 1 is a bar graph illustrating the effects of 1 mg/kg ( ), 5 mg/kg ( ) and 15 mg/kg ( ) doses of a representative estradiol-CDS, i.e. 17 β-[(1-methyl-1,4-dihydro-3-pyridinyl)carbonyloxy]estra-1,3,5(10)-trien-3-ol, on weight change relative to vehicle injected controls in intact male rats from 0 to 36 days post-treatment.

The term "weight control" is used herein in its conventional sense. Primarily, "weight control" used herein means reducing the body weight of an overweight mammal, especially of an obese mammal, preferably to ultimately achieve levels generally recognized as normal for the mammal in question. However, "weight control" also encompasses the concept of maintaining body weight at a normal level. The exact manner in which the methods and compositions of this invention function to achieve weight control has not yet been fully elucidated and is not critical to the invention. While the present inventors do not wish to be bound to any particular theory, it is thought that, at least initially, the method and compositions of this invention act to suppress appetite, thus reducing food intake. However, the instant method and compositions may also exercise control of body weight by more subtle means, such as by causing changes in metabolism and/or in locomotor activity. It is even possible that, by means of the present invention, the individual mammal's set-point for body weight may be readjusted to a lower, more nearly normal, limit.

The term "estrogen", e.g. as used in connection with formula (I), is also employed herein in its conventional sense and thus comprises the natural estrogens, the semi-synthetic estrogens and the synthetic estrogens. See, for example, *Cutting's Handbook of Pharmacology,* seventh edition, ed. T. Z. Cs/áky, M.D. and Byron A. Barnes, Ph.D., Appleton-Century-Crofts, Norwalk, Conn. 1984, Part 14, Chapter 35, pp. 427–432.

Preferred compounds for use in the method and compositions of this invention can be represented by the formula $$E [DHC]_n \qquad (Ia)$$

wherein E— is the residue of an estrogen containing at least one reactive hydroxyl functional group, said residue being characterized by the absence of a hydrogen atom from at least one of said reactive functional groups in said estrogen; n is a positive integer equal to the number of said functional groups from which a hydrogen atom is absent; and [DHC] is the reduced, biooxidizable, blood-brain barrier penetrating, lipoidal form of a dihydropyridinepyridinium salt redox carrier. In formula (Ia), n is preferably 1, 2 or 3, more preferably 1 or 2 and most preferably 1.

Among the estrogens whose derivatives of formulas (I) and (Ia) are intended for use in the method and compositions of this invention, there can be mentioned natural estrogens, i.e. estradiol and its 3- or 17-monesters such as estradiol benzoate, estradiol cypionate, estradiol enanthate, estradiol undecylate, estradiol valerate, estradiol propionate and estradiol undecenylate, as well as estrone and estriol; semisynthetic estrogens, for example ethinyl estradiol, mestranol, quinestrol, estrazinol, estrofurate and nylestriol; and synthetic estrogens, e.g. benzestrol, diethylstilbestrol, dienestrol and hexestrol. Preferably, the estrogenic portion of the compounds of formulas (I) and (Ia) has a steroidal structure, i.e. it is derived from a natural or semi-synthetic estrogen; more preferably, it is derived from a 3-monohydroxy, 17-monohydroxy or 3,17-dihydroxy steroid having an aromatic A-ring, a carrier moiety [DHC] replacing the monohydroxy group in the 3- or 17-monohydroxy steroid, and replacing one or both hydroxy groups in the 3,17-dihydroxy steroid. At the preset time, compounds derived from estradiol by replacement of one or both hydroxyl functions with carrier groupings are most especially preferred for use in the method and compositions of this invention.

The term "lipoidol" as used herein is intended to designate a carrier moiety which is lipid-soluble or lipophilic, as in the earlier Bodor patents and application referenced hereinabove.

The expression "non-toxic pharmaceutically acceptable salts" as used herein generally includes the non-toxic salts of the compounds of formulas (I) and (Ia) hereinabove formed with non-toxic, pharmaceutically acceptable inorganic or organic acids of the general formula HX. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, toluenesulfonic and the like. The expression "anion of a pharmaceutically acceptable organic or inorganic acid" as used herein, e.g. in connection with formula (II) hereinbelow, is intended to include anions of such HX acids.

It will be appreciated from the foregoing that a compound of formula (I) may be administered as the free base or in the form of a non-toxic pharmaceutically acceptable salt thereof, i.e. a salt which can be represented by the formula

[E—DHC].HX 

wherein the structural variables are defined as before; and that, regardless of the actual form in which the compound is administered, it will be converted in vivo to a quaternary salt of (II) hereinbelow, X$^-$ being present in vivo. It is not necessary that the anion be introduced as part of the compound administered. Indeed, even when the compound of formula (I) is used in its salt form, the anion of the formula (II) compound in vivo is not necessarily the same as that present in the formula (I) compound. In fact, the exact identity of the anionic portion of the compound of formula (II) is immaterial to the in vivo transformation of (I) to (II).

The compounds of formula (I) which are employed in the method and compositions of the present invention can be synthesized by methods described in the aforementioned Bodor U.S. Pat. Nos. 4,479,932 and 4,540,564 and U. of Florida PCT/US83/00725 (International Publication No. WO83/03968). Synthesis generally begins with preparation of the corresponding quaternary intermediates of the formula $$[E-QC^+]X^- \quad (II)$$

wherein $X^-$ is the anion of a non-toxic pharmaceutically acceptable acid, [E] is an estrogen and $[QC^+]$ is the hydrophilic, ionic pyridinium salt form of a dihydropyridine⇌pyridinium salt redox carrier. In the case of preparation of the preferred compounds of formula (Ia), the corresponding quaternary intermediates have the formula $$E[QC^+]_n qX^{-t} \quad (IIa)$$

wherein E— and n are as defined with formula (Ia); $[QC^+]$ and $X^-$ are as defined with formula (II); t is the valence of the acid anion; and q is the number which when multiplied by t is equal to n. The pyridinium salts of formulas (II) and (IIa) are not only chemical intermediates to the corresponding compounds of formulas (I) and (Ia), respectively, but also represent the form of the chemical delivery system which is "locked in" the brain following administration of the dihydro derivative.

The preparation of the intermediates of formula (II) is tailored to the particular estrogen portion and carrier portion to be combined, especially to the nature of the chemical bond between them and the presence or absence of other reactive functional groups, which may need to be protected during particular stages of the synthetic pathway. In forming the intermediates of formula (I), at least one reactive functional group, for example a hydroxyl, amino, mercapto, amide or imide group, in the estrogen will be bonded to $[QC^+]$, the hydrophilic, ionic pyridinium salt form of a dihydropyridine⇌pyridinium salt redox carrier.

It will be appreciated that by "dihydropyridine carrier" or "[DHC]", there is intended any non-toxic carrier moiety comprising, containing or including the dihydropyridine nucleus, whether or not a part of any larger basic nucleus, and whether substituted or unsubstituted, the only criteria therefor being capacity for penetration of the blood-brain barrier (BBB) and in vivo oxidation thereof to the corresponding quaternary pyridinium salt carrier $[QC^+]$. As aforesaid, the ionic pyridinium salt estrogen/carrier prodrug entity $[E-QC^+]$ which result from such in vivo oxidation is prevented from efflux from the brain, while elimination from the general circulation is accelerated. Subsequently, the bond coupling the estrogen species to the quaternary carrier $[QC^+]$ is metabolically cleaved, which results in sustained delivery of the estrogen in the brain and facile elimination of the carrier moiety $[QC^+]$. And the cleavage of the quaternary compound (II) to sustainedly deliver the estrogen in the brain with concomitant facile elimination of the carrier moiety $[QC^+]$ is characteristically enzymatic cleavage, e.g., by esterase, peptidase, amidase, cholinesterase or hydrolytic enzyme, albeit any type of in brain cleavage which might result, whether enzymatic, metabolic or otherwise, of course remains within the ambit of the delivery system.

Many different dihydropyridine⇌pyridinium salt redox carrier moieties are disclosed in the earlier Bodor patents and application referenced hereinabove. Obviously, the choice of carrier will be at least partially dictated by the structure of the estrogen selected for derivatization. Most estrogens contain at least one free hydroxyl group which can be conveniently linked to a carrier moiety to give the intermediates of formula (IIa) and, ultimately, the compounds of formula (Ia). The following major classes of quaternaries are prime examples of the carrier moieties encompassed hereby for linkage to an estrogen having at least one hydroxyl functional grouping, replacing a hydrogen atom from at least one of said functional groupings with one of the following $[QC^+]$ groupings:

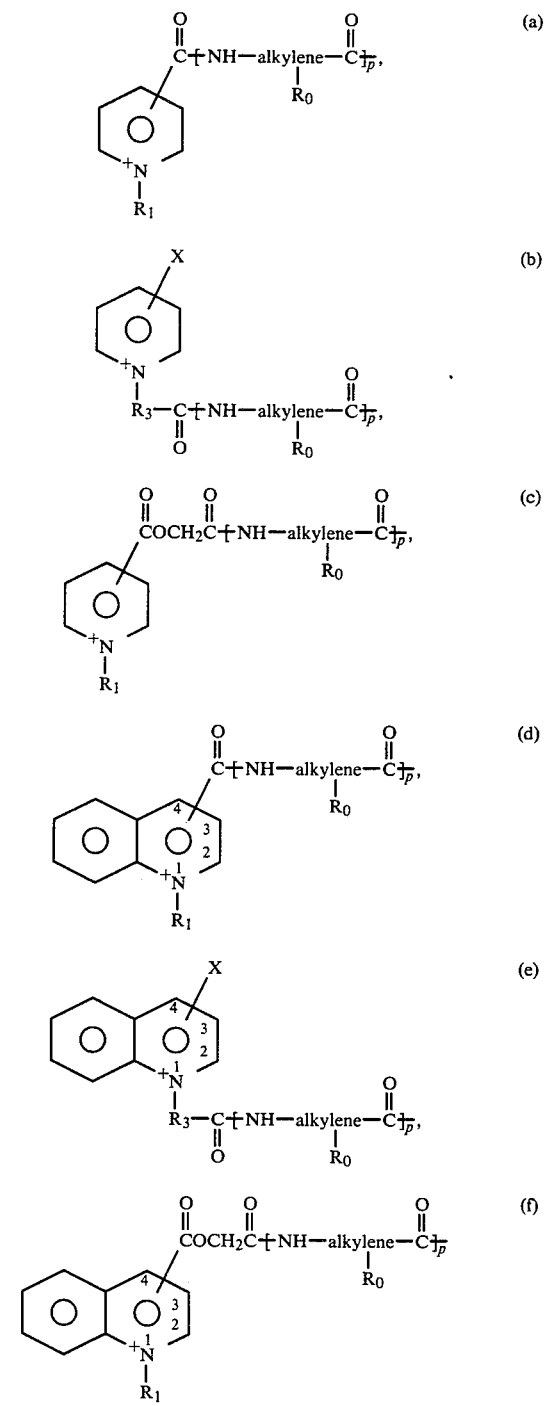

-continued

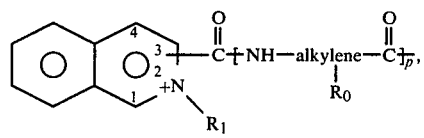
(g)

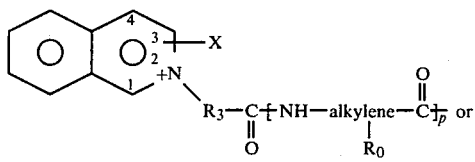
(h)

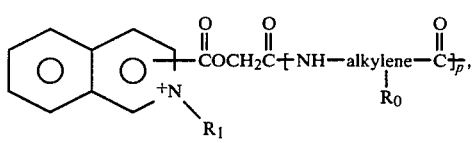
(j)

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a) and (c) and the X substituent in formula (b) can each be attached at the 2, 3 or 4 position of the pyridinium ring; the carbonyl-containing groupings in formulas (d) and (f) and the X substituent in formula (e) can each be attached at the 2, 3 or 4 position of the quinolinium ring; and the carbonyl-containing groupings in formulas (g) and (j) and the X substituent in formula (h) can each be attached at the 1, 3 or 4 position of the isoquinolinium ring.

Here and throughout this application, the expression "$C_1$-$C_7$ haloalkyl" means $C_1$-$C_7$ alkyl substituted by one or more halogen atoms. Also here and throughout this application, the alkyl radicals, including alkyl and alkylene portions of other radicals, can be straight or branched unless otherwise specified.

The expression "$R_o$ is a radical identical to the corresponding portion of a natural amino acid" is believed to be self-explanatory. Thus, for example, $R_o$ can be hydrogen, as in glycine; methyl, as in alanine; —CH(CH$_3$)$_2$, as in valine; —CH$_2$—CH(CH$_3$)$_2$, as in leucine;

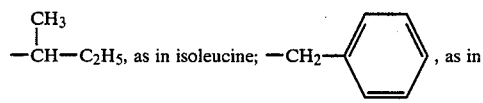

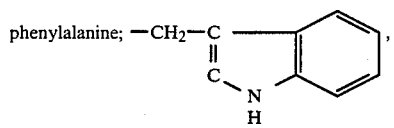

as in tryptophan; —CH$_2$OH, as in serine; —CH(OH)—CH$_3$, as in threonine; —(CH$_2$)$_2$—SCH$_3$, as in methionine; —CH$_2$—CONH$_2$, as in asparagine; —CH$_2$CH$_2$—CONH$_2$, as in glutamine;

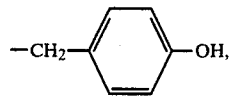

as in tyrosine; —CH$_2$SH, as in cysteine; —CH$_2$COOH, as in aspartic acid; and —CH$_2$CH$_2$COOH, as in glutamic acid. The expression "natural amino acid" as used herein does not encompass dopa or L-DOPA. Preferred amino acids encompassed by the $R_o$ term include glycine, alanine, valine, leucine, phenylalanine, isoleucine, methionine, asparagine and glutamine.

The dihydro forms [DHC] corresponding to the aforementioned quaternaries are as follows:

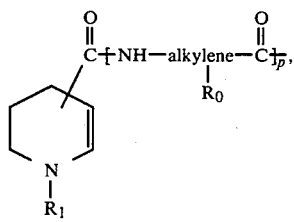
(a')

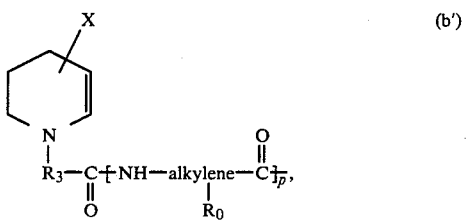
(b')

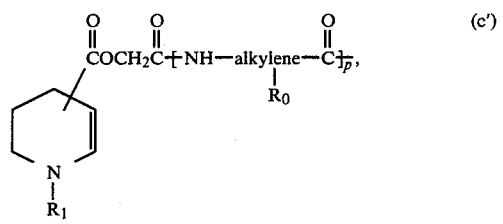
(c')

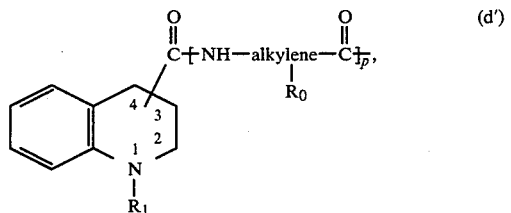
(d')

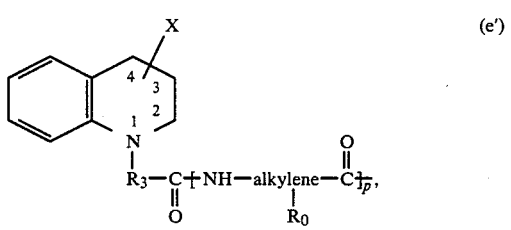
(e')

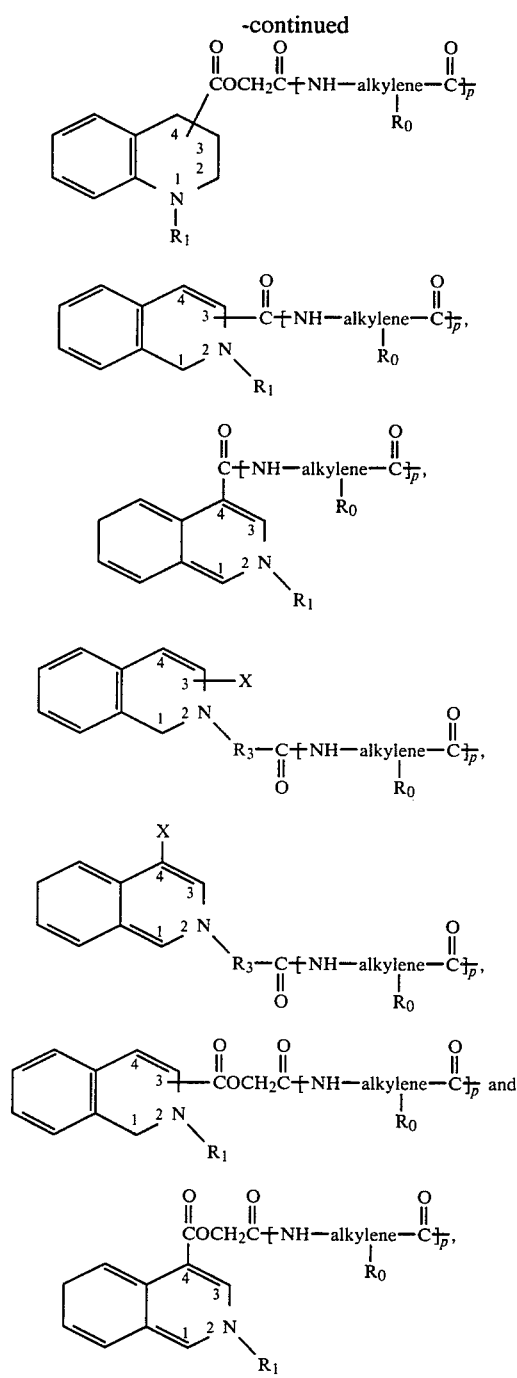

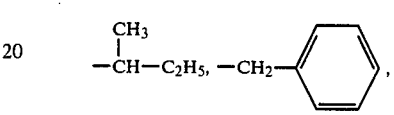

wherein the alkylene group can be straight or branched and can contain 1 to 3 carbon atoms; $R_o$ is radical identical to the corresponding portion of a natural amino acid; p is 0, 1 or 2, provided that, when p is 2, then the alkylene groups can be the same or different and the $R_o$ radicals can be the same or different; the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihydroquinoline ring; $R_1$ is $C_1$–$C_7$ is alkyl, $C_1$–$C_7$ haloalkyl or $C_7$–$C_{10}$ aralkyl; $R_3$ is $C_1$–$C_3$ alkylene; X is —CONR'R" wherein R' and R", which can be the same or different, are each H or $C_1$–$C_7$ alkyl, or X is —CH=NOR''' wherein R''' is H or $C_1$–$C_7$ alkyl; the carbonyl-containing groupings in formulas (a') and (c') and the X substituent in formula (b') can each be attached at the 2, 3 or 4 position of the dihydropyridine ring; the carbonyl-containing groupings in formulas (d') and (f') and the X substituent in formula (e') can each be attached at the 2, 3 or 4 position of the dihydroquinoline ring; and the carbonyl-containing gorupings in formulas (g') and (j') and the X substituent in formula (h') can each be attached at the 1, 3 or 4 position of the dihydroisoquinoline ring.

The presently preferred dihydropyridine⇌pyridinium salt redox carrier moieties for use herein are those wherein p is 0 or 1, most preferably 0; alkylene, when present (i.e. p=1 or 2), is —CH$_2$—; $R_o$, when present (i.e. p=1 or 2), is H, —CH$_3$, —CH(CH$_3$)$_2$, —CH$_2$—CH(CH$_3$)$_2$, —(CH$_2$)$_2$—SCH$_3$, —CH$_2$—CONH$_2$ or —CH$_2$CH$_2$—CONH$_2$; $R_1$, when present, is —CH$_3$; $R_3$, when present, is —CH$_2$CH$_2$—; X, when present, is —CONH$_2$; the depicted carbonyl-containing groupings in formulas (a) and (c) and the X substituent in formula (b) are attached at the 3-position; the depicted carbonyl-containing groupings in formulas (d) and (f) and the X substituent in formula (e) are attached at the 3-position; and the depicted carbonyl-containing groupings in formulas (g) and (j) and the X substituent in formula (h) are attached at the 4-position; and the corresponding dihydro forms.

Especially preferred dihydropyridine⇌pyridinium salt redox carrier moieties are the quaternaries of structures (a), (b), (d), (e), (g) and (h); and the corresponding dihydro forms, most especially when they contain the preferred structural variables identified in the preceding paragraph.

Various illustrative synthetic schemes as applied to specific compounds for use herein are set forth below in the sections entitled ILLUSTRATIVE SYNTHETIC METHODS and SYNTHETIC EXAMPLES. (Yet other methods are disclosed in the aforementioned earlier Bodor patents and application.) While the sequence of reaction steps can be varied in many cases, in general the final step (except in the case of optional salt formation) will be reduction of a quaternary compound of formula (II) to the corresponding dihydro compound of formula (I). The reduction is usually conducted at a temperature from about $-10°$ C. to room temperature, for a period of time from about 10 minutes to 2 hours, conveniently at atmospheric pressure. Typically, a large excess of reducing agent is employed, e.g. a 1:5 molar ratio of reducing agent to starting compound of formula (II). The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product of formula (I) is usually insoluble in water and thus can be readily separated from the reaction medium. In the case of sodium borohydride reduction, an organic reaction medium is employed, e.g. a lower alkanol such as methanol, an aqueous alkanol or other protic solvent.

ILLUSTRATIVE SYNTHETIC METHODS

I. Methods for Derivatizing —OH Functions in Estrogens with p=0 Type Carriers

METHOD A

The estrogen is reacted with nicotinoyl chloride, with nicotinic anhydride, or with nicotinic acid in the presence of a suitable coupling agent such as dicyclohexylcarbodiimide, in an appropriate organic solvent, to afford the corresponding nicotinate. The nicotinate is then quaternized, typically by treatment with methyl iodide in a suitable organic solvent, to afford the quaternary derivative of formula (II), which is then reduced by treatment with sodium dithionite or sodium borohydride as generally described hereinabove to afford the desired compound of formula (I). When the estrogen contains more than one reactive hydroxyl function, reaction conditions may be varied so that more than one hydroxyl function will be converted to nicotinate groupings. If more than one carrier moiety is so introduced, selective hydrolysis may be employed at a later stage, e.g. after quaternization, to generate a derivative containing fewer carrier moieties, if such is desired. The representative estrogens depicted below may be derivatized in this manner to the corresponding compounds of formulas (II) and (I). 3-Monoesters and 17-monoesters of estradiol, e.g. estradiol benzoate and estradiol valerate, and estriol may be similarly derivatized, as may the other hydroxy-containing estrogens specifically mentioned in this specification.

The foregoing procedure may be repeated using picolinic acid or its acid chloride or anhydride, or isonicotinic acid or its acid chloride or anhydride, in place of nicotinic acid or its acid chloride or anhydride, respectively, to convert drugs such as those specifically mentioned for derivatizing by this method to the corresponding picolinates and isonicotinates and then to the corresponding compounds of formulas (II) and (I).

Alternatively, the estrogen may be reacted with an activated ester of nicotinic acid, picolinic acid or isonicotinic acid, e.g. a succinimidyl ester such as

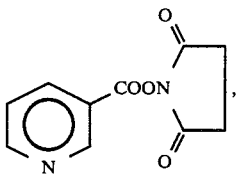

and the procedure described above repeated to afford the identical products. As yet another alternative, the activated ester, e.g. the succinimidyl ester depicted above, may be quaternized (e.g. by treatment with methyl iodide) and the quaternized activated ester then reacted with the estrogen. The quaternary compound of formula (II) thus obtained may then be reduced as described in the first paragraph of this method to give the corresponding compound of formula (I).

| STARTING MATERIAL | QUATERNARY INTERMEDIATE (CATION) | DIHYDRO DERIVATIVE |
|---|---|---|
| 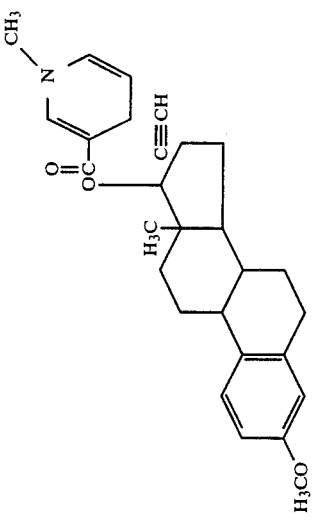 mestranol | 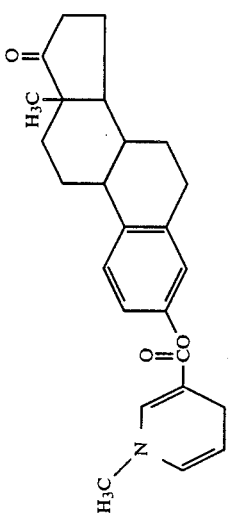 | 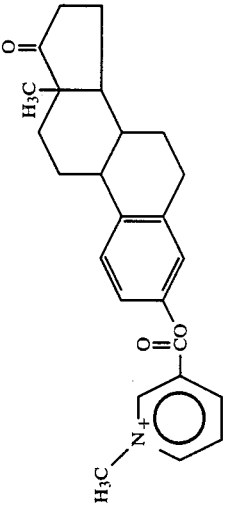 |
| 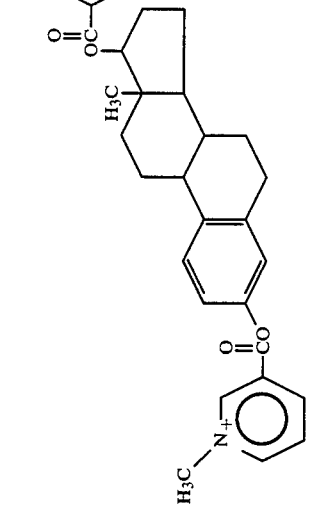 estrone | 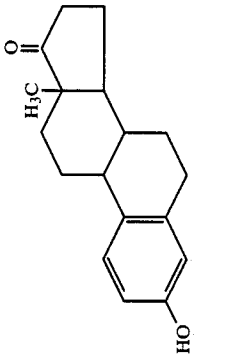 | 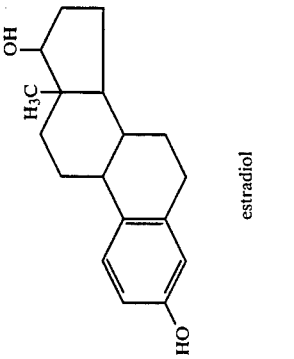 |
| estradiol | | |
This compound can be selectively hydrolyzed by known methods to the corresponding 17-monoester, which can be reduced to give the preferred 17-monoester of formula (I).

| STARTING MATERIAL | QUATERNARY INTERMEDIATE (CATION) | DIHYDRO DERIVATIVE |
|---|---|---|
| benzestrol | | |
| ethinyl estradiol | | |
| diethylstilbestrol | | |

METHOD B

This is an alternate process for derivatizing estrogens containing secondary or tertiary hydroxyl functional groups with p=0 type carriers. According to this process, the estrogen is reacted with chloral or other aldehyde capable of forming a hemiacetal therewith. In the case of chloral, this converts the —OH function(s) to

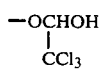

groupings. The —OH function(s) of the resultant hemiacetal can then be derivatized by any of the methods for derivatizing —OH groups disclosed herein, e.g. by reaction with nicotinic acid or its acid chloride or anhyride as described in Method A.

This process is of particular value when the —OH group(s) in the estrogen is/are sterically hindered and-/or when it is desired to alter the rate of release of the estrogen from that obtained when the carrier is hooked directly to the estrogen's hydroxy function(s).

The representative estrogen depicted below may be derivatized in ths manner to the corresponding compounds of formulas (II) and (I). Other estrogens containing secondary or tertiary —OH groups which are disclosed herein, e.g. in connection with Method A, may be similarly derivatized. This method is of special interest for derivatizing steroidal estrogens containing secondary or tertiary 17 β-hydroxy substituents, especially such hormones bearing a bulky 17 α-substituent such as a 17 α-ethynyl grouping.

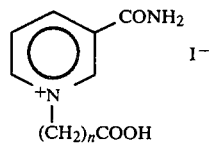

wherein n=1–3, preferably 2, is used in place of nicotinic acid. (That starting material may be prepared from nicotinamide, e.g. when n=2, by reacting 3-iodopropionic acid with nicotinamide). The quaternary salt of formula (II) thus obtained may then be reduced as described in Method A.

The representative estrogen depicted below may be derivatized in this manner to the corresponding compounds of formulas (II) and (I), as may the remaining estrogens mentioned with Method A.

Method C may be of particular use in preparing derivatives of estrogens in which the hydroxy function is hindered, e.g. mestranol.

Alternatively, Method C may follow Method A except that it employs a reactant of the formula

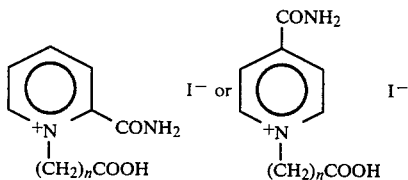

prepared from picolinamide or isonicotinamide, e.g.

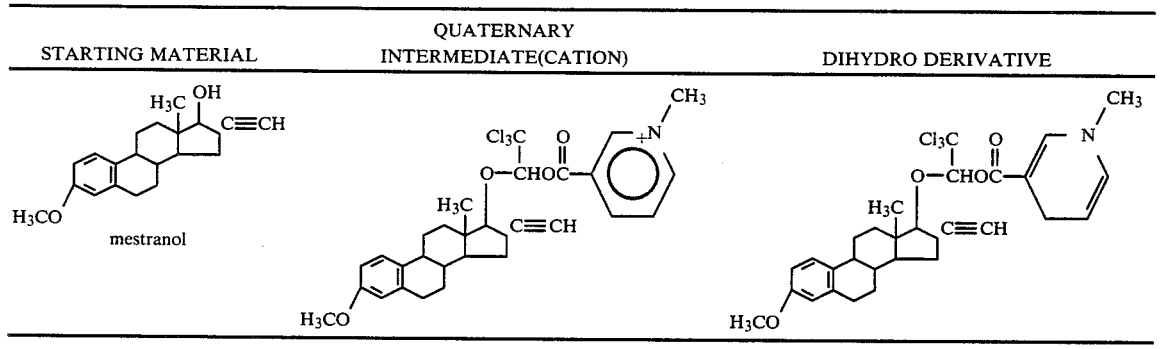

METHOD C

Method A is followed, except that a reactant of the formula when n=2, by reacting 3-iodopropionic acid with the selected amide starting material), to afford derivatives of the estrogens indicated with Method A.

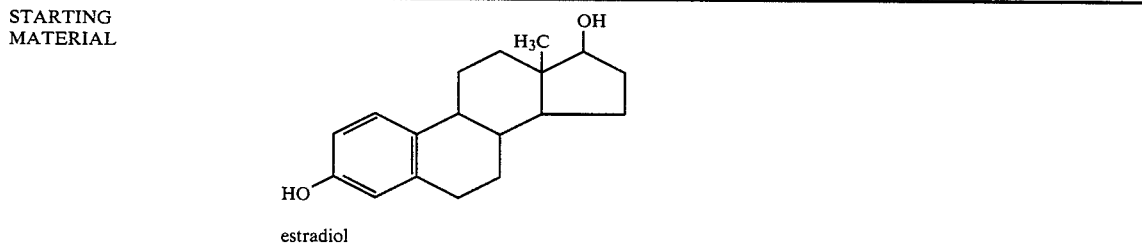

QUATERNARY INTERMEDIATE(CATION)

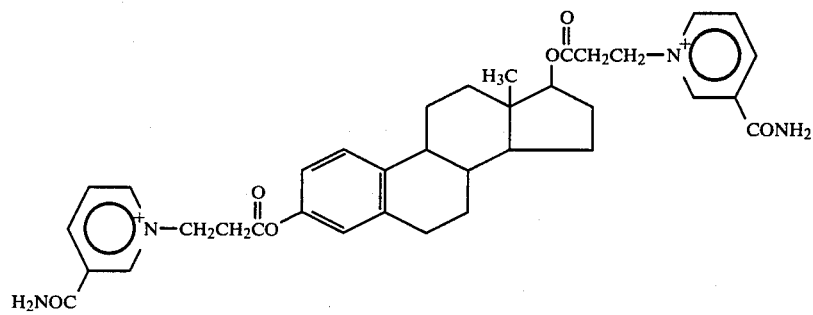

This compound can be subsequently selectively hydrolyzed by known methods to the corresponding 17-monoester of formula (II), which can be reduced to the corresponding preferred 17-monoester of formula (I).

DIHYDRO DERIVATIVE

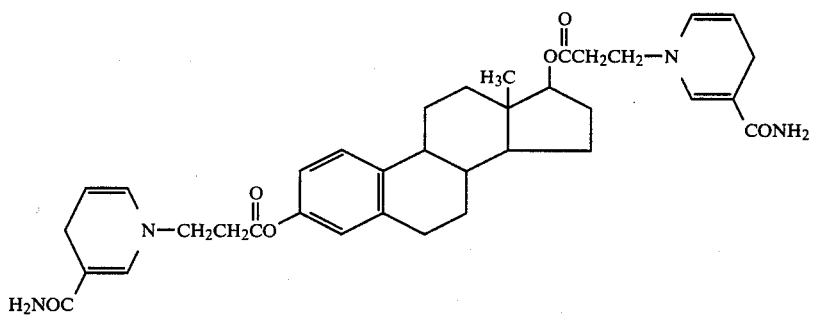

METHOD D

Method A is followed, except that the drug is reacted with 3-quinolinecarboxylic acid or its acid chloride or anhydride or activated ester or quaternized activated ester instead of nicotinic acid or its acid chloride or anhydride or activated ester or quaternized activated ester.

The representative drugs depicted below may be derivatized in this manner to the corresponding compounds of formulas (II) and (I), as may the remaining drugs mentioned with Method A.

The procedure of Method D may be repeated using 4-isoquinolinecarboxylic acid or its acid chloride or anhydride or activated ester or quaternized activated ester in place of 3-quinolinecarboxylic acid or its acid chloride or anhydride or activated ester or quaternized activated ester, to afford the corresponding derivatives of estrogens such as those indicated with Method A.

The general procedures described above may be utilized to provide the 1,2-dihydro derivatives as well as the depicted 1,4-dihydros.

| STARTING MATERIAL | QUATERNARY INTERMEDIATE (CATION) | DIHYDRO DERIVATIVE |
|---|---|---|
| estradiol | | |
| mestranol | | |

This compound can be subsequently selectively hydrolyzed by known methods to the corresponding 17-monoester of formula (II), which can be reduced to the corresponding preferred 17-monoester of formula (I).

METHOD E

| | |
|---|---|
| STARTING MATERIAL | 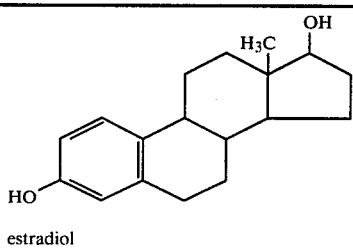 estradiol |
| QUATERNARY INTERMEDIATE(CATION) | 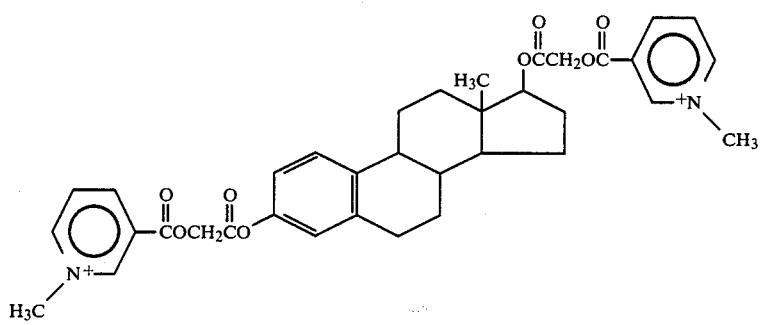 |
| DIHYDRO DERIVATIVE | 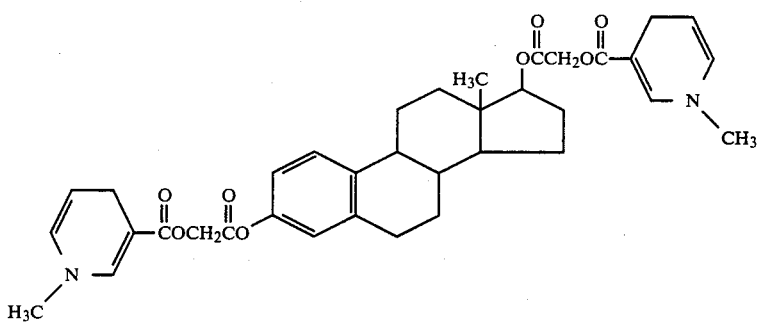 |

This compound can be subsequently selectively hydrolyzed by known methods to the corresponding 17-monoester of formula (II), which can be reduced to the corresponding preferred 17-monoester of formula (I).

Method A is followed, except that a reactant of the formula

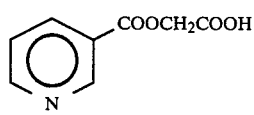

is used in place of nicotinic acid. (That starting material may be prepared by reacting nicotinic anhydride, nicotinoyl chloride or nicotinic acid with glycolic acid.)

The representative estrogen mentioned below may be derivatized in this manner to the corresponding compounds of formulas (II) and (I), as may the remaining estrogens mentioned with Method A.

Alternatively, Method E may follow Method A except that it employs a reactant of the formula

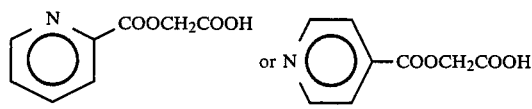

(prepared by reacting picolinic acid or its acid chloride or anhydride, or isonicotinic acid or its acid chloride or anhydride, respectively, with glycolic acid), to afford derivatives of the estrogens indicated with Method A.

II. Method for Derivatizing —OH Functions in Estrogens with p=1 or p=2 Type Carriers

METHOD F

The estrogen is reacted with nicotinuric acid chloride, with nicotinuric acid anhydride, or with niotinuric acid in the presence of a suitable coupling agent such as dicyclohexylcarbodiimide, in an appropriate organic solvent, to afford the corresponding glycylnicotinate, or nicotinurate. The nicotinurate is then quaternized and subsequently reduced using the methods described above in Method A. When the estrogen contains more than one reactive hydroxyl function, reaction conditions may be varied so that more than one hydroxyl function will be converted to nicotinurate groupings. If more than one carrier moiety is so introduced, selective hydrolysis may be employed at a later stage in the synthetic pathway, e.g. after quaternization, to generate a derivative containing fewer carrier moieties, if such is desired.

Alternatively, the estrogen may be reacted with an activated ester of nicotinuric acid or the like, e.g. a succinimidyl ester such as

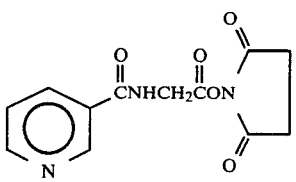

and the product quaternized and then reduced as described above. As yet another alternative, the activated ester, e.g. the succinimidyl ester depicted above, may be quaternized (e.g. by treatment with methyl iodide) and the quaternized activated ester then reacted with the estrogen. The quaternary compound of formula (II) thus obtained may then be reduced as described in Method A to give the corresponding compound of formula (I).

Alternatively, glycine may be first reacted with a reagent capable of introducing an amino protecting group such as benzyloxycarbonyl or t-butylcarbonyl and the N-protected glycine then reacted with the estrogen in the presence of a coupling agent such as dicyclohexylcarbodiimide, followed by removal of the N-protecting group, followed by reaction with nicotinoyl chloride or nicotinic anhydride, or with nicotinic acid in the presence of dicyclohexylcarbodiimide or other suitable coupling agent, to afford the nicotinurate. The nicotinurate may then be quaternized and the quaternary reduced as described in the preceding paragraph.

The representative estrogens depicted below may be derivatized in this manner to the corresponding compounds of formulas (II) and (I). Estriol and 3-monoesters and 17-monoesters of estradiol, e.g. estradiol benzoate and estraidol valerate, may be similarly derivatized, as may the other hydroxy-containing estrogens specifically mentioned in this specification.

The procedure of the third paragraph of this method may be repeated using picolinic acid or its acid chloride or anhydride, or isonicotinic acid or its acid chloride or anhydride, in place of nicotinic acid or its acid chloride or anhydride, respectively, to convert estrogens such as those specifically mentioned for derivatizing by this method to the corresponding glycyl picolinic acid esters or glycyl isonicotinic acid esters and then to the corresponding compounds of formulas (II) and (I). The procedure of the first or second paragraph of this method may be similarly adapted. Moreover, any of these procedures, may be repeated, substituting a different amino acid or nicotinic acid derivative thereof for the glycine or nicotinuric acid used above, e.g. replacing glycine with alanine, valine, leucine, phenylalanine, isoleucine, methionine, asparagine or glutamine.

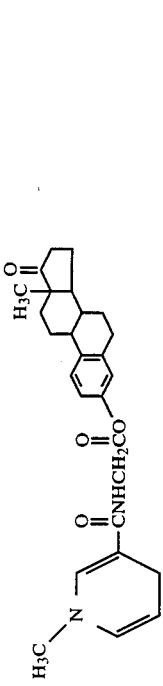

| STARTING MATERIAL | QUATERNARY INTERMEDIATE (CATION) | DIHYDRO DERIVATIVE |
|---|---|---|
| quinestrol | | |

This compound can be subsequently selectively hydrolyzed by known methods to the corresponding 17-monoester of formula (II), which can be reduced to the corresponding preferred 17-monoester of formula (I).

METHOD G

This is an alternate process for derivatizing estrogens containing secondary or tertiary hydroxyl functional groups with p=1 or 2 type carriers. According to this process, the estrogen is reacted with chloral or other aldehyde capable of forming a hemiacetal therewith. In the case of chloral, this converts the —OH function(s) to

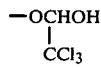

groupings. The —OH function(s) of the resultant hemiacetal can then be derivatized by any of the methods for derivatizing —OH groups disclosed herein, e.g. by reaction with nicotinuric acid or its acid chloride or anhydride as described in Method F.

This process is analogous to Method B hereinabove and is of particular interest in connection with estrogens of the types described in paragraphs 2 and 3 of Method B.

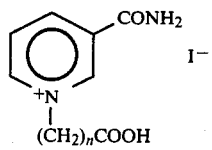

wherein n=1-3, preferably 2 (prepared as described in Method C), is used in place of nicotinic acid. The quaternary salt of formula (II) thus obtained may then be reduced as described in Method A.

The representative estrogens depicted below may be derivatized in this manner to the corresponding compounds of formulas (II) and (I), as may the remaining estrogens indicated with Method C.

Alternatively, Method H may follow Method F, third paragraph, except that it employs a reactant of the formula

STARTING MATERIAL

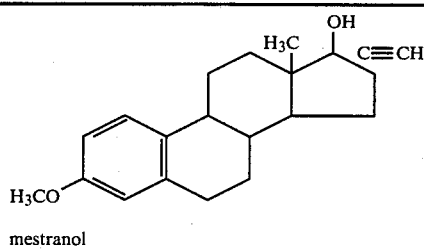

mestranol

QUATERNARY INTERMEDIATE(CATION)

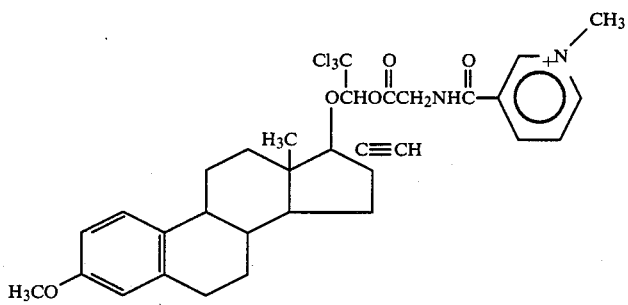

DIHYDRO DERIVATIVE

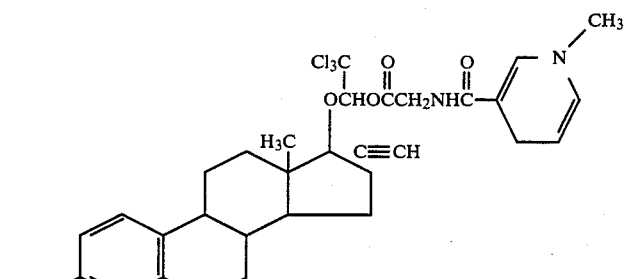

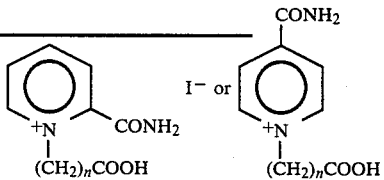

METHOD H

The procedure of the third paragraph of Method F is followed, except that a reactant of the formula (prepared as described in Method C) in place of nicotinic acid, to afford derivatives of the drugs indicated with Method C.

The procedures of this method may be repeated, substituting a different amino acid, e.g. alanine, valine, leucine, phenylalanine, isoleucine, methionine, asparagine or glutamine, for the glycine used in the first step. (See Method F, third paragraph).

The representative estrogens depicted below may be derivatized in this manner to the corresponding compounds of formulas (II) and (I), as may the remaining estrogens mentioned with Method F.

The procedure of Method I may be repeated using 4-isoquinolinecarboxylic acid or its acid chloride or anhydride in place of 3-quinolinecarboxylic acid or its acid chloride or anhydride, to afford the corresponding derivatives.

The general procedures described above may be utilized to provide the 1,2-dihydro derivatives as well as the depicted 1,4-dihydros.

| STARTING MATERIAL | |
|---|---|
| 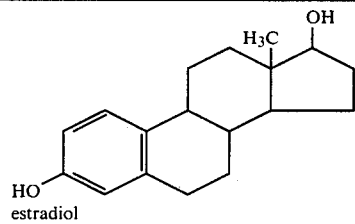 estradiol | |
| QUATERNARY INTERMEDIATE (CATION) | 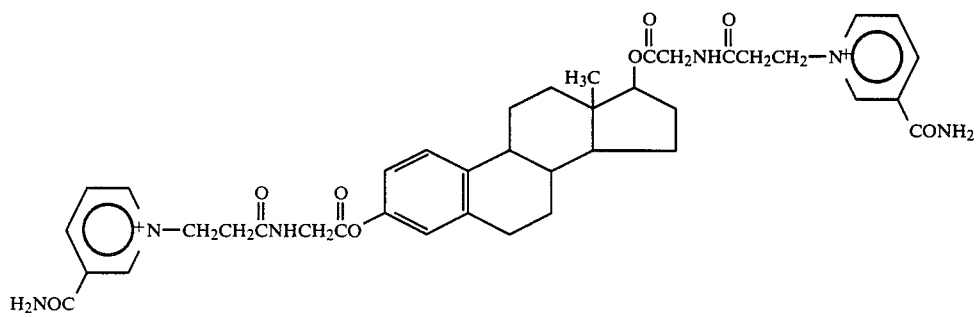 This compound can be subsequently selectively hydrolyzed by known methods to the corresponding 17-monoester of formula (II), which can be reduced to the corresponding preferred 17-monoester of formula (1). |
| DIHYDRO DERIVATIVE | 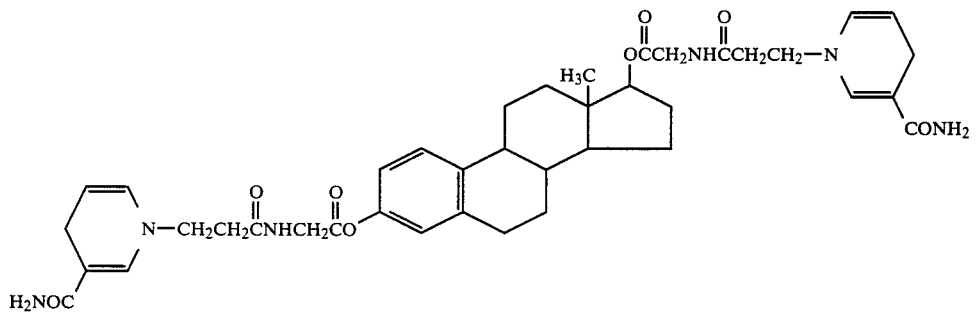 |

METHOD I

The procedure of Method F, third paragraph, is followed, except that removal of the N-protecting group is followed by reaction with 3-quinolinecarboxylic acid or its acid chloride or anhydride instead of nicotinic acid or its acid chloride or anhydride.

| STARTING MATERIAL | QUATERNARY INTERMEDIATE(CATION) |
|---|---|
| 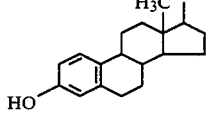 estradiol | 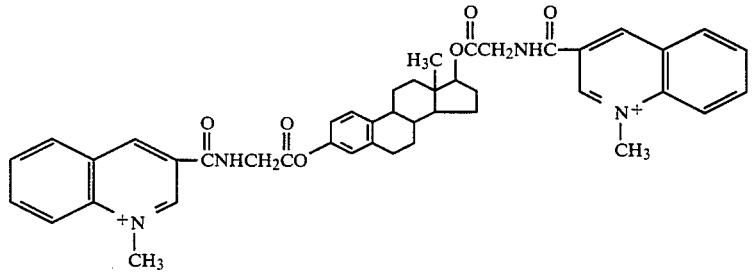 This compound can be subsequently selectively hydrolyzed by known methods to the corresponding 17-monoester of formula (II), which can be reduced to the corresponding preferred 17-monoester of formula (I). |

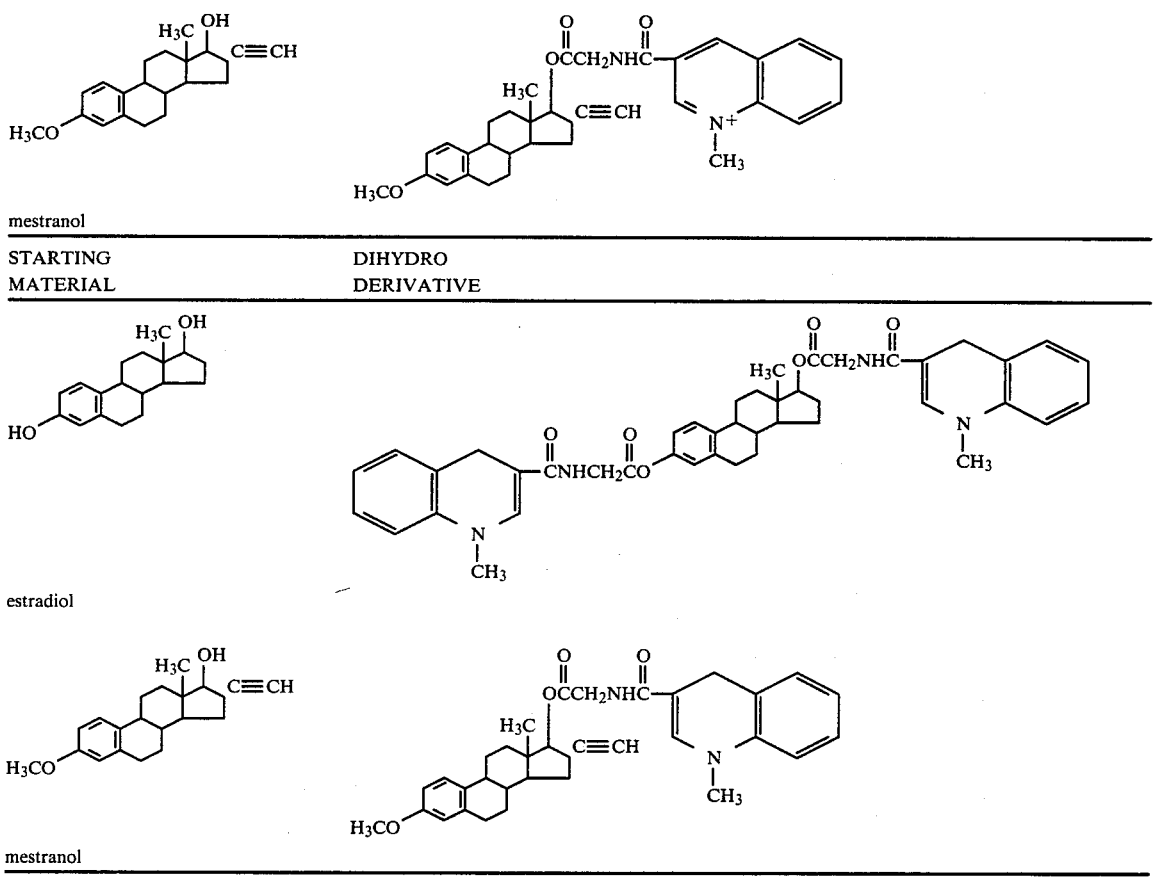

mestranol

| STARTING MATERIAL | DIHYDRO DERIVATIVE | estradiol mestranol

METHOD D

The procedure of the third paragraph of Method F is followed, except that a reactant of the formula

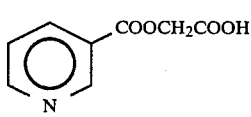

is used in place of nicotinic acid.

The representative estrogen depicted below may be derivatized in this manner to the corresponding compounds of formulas (II) and (I), as may the remaining estrogens mentioned with Method F.

Alternatively, Method J may follow Method F, third paragraph, except that it employs a reactant of the formula

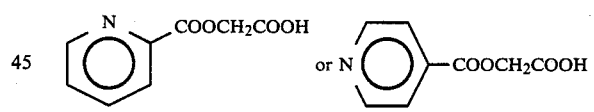

(prepared as described in Method E), to afford derivatives of the estrogens indicated with Method F.

The procedure of the first or third paragraph of this method may be repeated, substituting a different amino acid, e.g. alanine, valine, leucine, phenylalanine, isoleucine, methionine, asparagine or glutamine, for the glycine used in the first step. (See Method F, third paragraph).

STARTING MATERIAL

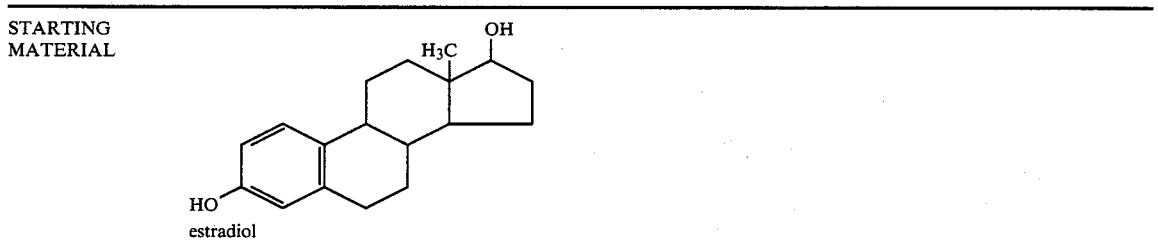

estradiol

| QUATERNARY INTERMEDIATE (CATION) | 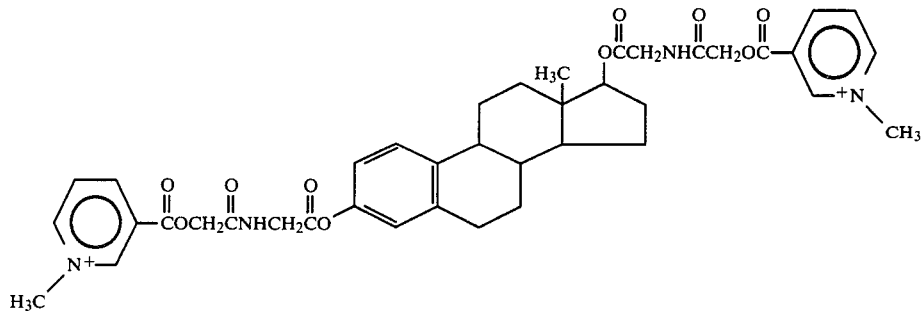 |
|---|---|

This compound can be subsequently selectively hydrolyzed by known methods to the corresponding 17-monoester of formula (II), which can be reduced to the corresponding preferred 17-monoester of formula (I).

| DIHYDRO DERIVATIVE | 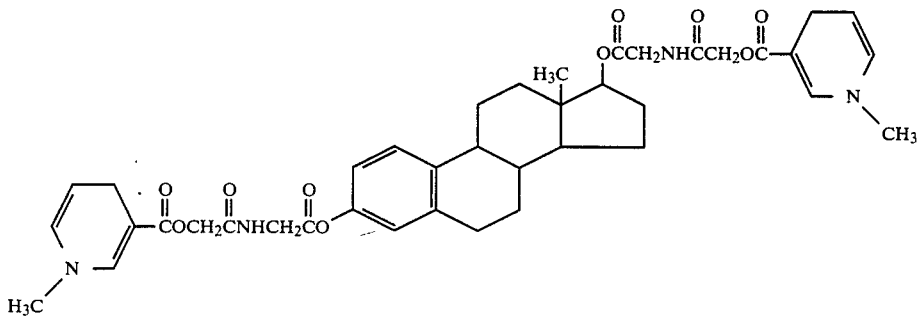 |
|---|---|

III. Method for Salt Formation

An ether solution of a compound of formula (I) is treated with an equivalent amount of anhydrous p-toluenesulfonic acid dissolved in dry ether. Mixing at room temperature is continued until the imminium salt precipitates out of solution. The salt is then removed by filtration.

SYNTHETIC EXAMPLES

In order to further illustrate the compounds useful in the method and compositions of this invention, the following synthetic examples are given, it being understood that the same are intended only as illustrative.

In the examples immediately to follow, all melting points were taken on a Mel-Temp apparatus and are not corrected. Elemental analyses were preformed at Atlantic Microlabs, Inc., Atlanta, Ga.

EXAMPLE 1

Preparation of 3-Nicotinoyloxyestra-1,3,5(10)-trien-17-one (Estrone Nicotinate)

To nicotinic acid (41 g, 0.333 mol) at 0° C. was added thionyl chloride (115 ml, 1.58 mol) with stirring. The mixture was refluxed for one hour, and the white crystalline product was filtered and washed sparingly with dry benzene. Excess thionyl chloride was azeotroped off with dry benzene immediately before use. Yield 90% (53.97 g) of nicotinoyl chloride hydrochloride; NMR, IR identical with literature values.

To nicotinoyl chloride hydrochloride (2.65 g, 0.015 mol) in pyridine (20 ml) at 0° C. was added estrone (2 g, 0.0074 mol). The mixture was refluxed for one hour and then poured over 100 ml of ice cold water, filtered, and dried over $P_2O_5$ under vacuum. Yield 72% (2.0076 g), m.p. 207°–210° C. Anal. calculated for $C_{24}H_{25}NO_3$; C, 76.76; H, 6.72; N, 3.73. Found: C, 76.37; H, 6.96; N, 3.67.

The product is further characterized by the structural formula:

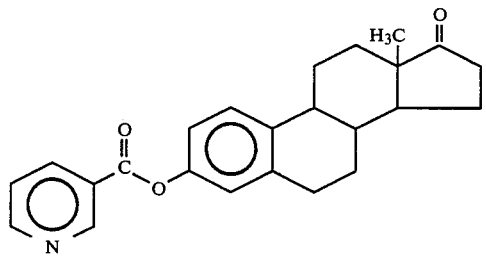

EXAMPLE 2

Preparation of 3-[(1-Methyl-3-pyridinium)carbonyloxy]estra-1,3,5(10)-trien-17-one iodide To estrone nicotinate (0.5 g, 0.0013 mol) in acetone (20 ml) was added methyl iodide (1 ml, 0.016 mol) and the mixture was refluxed overnight. The deep yellow precipitate was filtered, washed with acetone, and dried. Yield 90% (0.6226 g); m.p. 245°–248° C. (dec.). Anal. calculated for $C_{25}H_{28}NO_3I$: C, 58.03; H, 5.47; N, 2.71. Found: C, 58.16; H, 5.51; N, 2.67. The product has the formula:

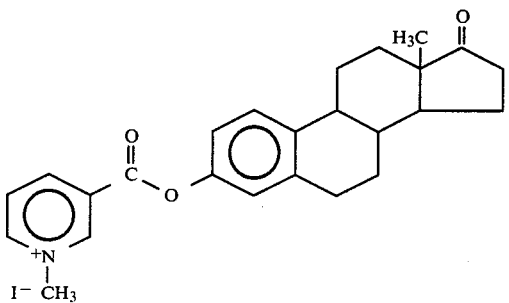

EXAMPLE 3

Preparation of 3-[(1-Methyl-1,4-dihydro-3-pyridinyl)carbonyloxy]estra-1,3,5(10)-trien-17-one To 3-[(1-methyl-3-pyridinium)carbonyloxy]estra-1,3,5(10)-trien-17-one iodide (0.600 g, 1.16 mmol) in a 50:50 mixture of methanol and deaerated water (80 ml) were added NaHCO$_3$ (0.58 g, 7.0 mmol) and Na$_2$S$_2$O$_4$ (0.81 g, 4.6 mmol). The mixture was stirred under N$_2$ for 2 hours. The precipitate was filtered, dissolved in methanol at room temperature, filtered, and then reprecipitated with deaerated water. This precipitate was then filtered and dried over P$_2$O$_5$ under vacuum. Yield 67% (0.3029 g). The product decomposes over the range 130°–180° C. Anal. calculated for C$_{25}$H$_{29}$NO$_3$ (+½H$_2$O): C, 74.96; H, 7.56; N, 3.50. Found: C, 75.44; H, 7.27; N, 3.38. The product is further characterized by the structural formula:

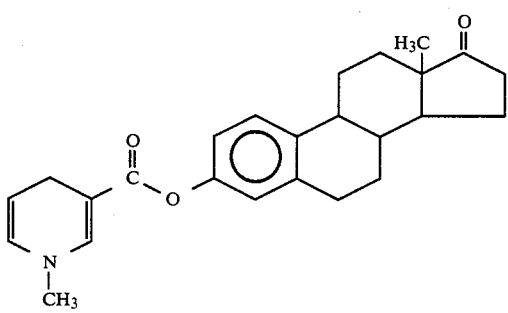

EXAMPLE 4

Preparation of 17β-Nicotinoyloxyestra-1,3,5(10)-trien-3-ol 3-methyl ether

To nicotinoyl chloride hydrochloride (3.15 g, 0.017 mol) in pyridine (20 ml) at 0° C. was added estradiol 3-methyl ether (2 g, 0.0070 mol). After refluxing one hour, the mixture was poured over 100 ml of ice water, filtered and dried over P$_2$O$_5$ under vacuum. Yield 76% (2.0674 g), m.p. 140°–142° C. Anal. calculated for C$_{25}$H$_{29}$NO$_3$: C, 76.68; H, 7.48; N, 3.58. Found: 76.49; H, 7.50; N, 3.55. The product has the formula:

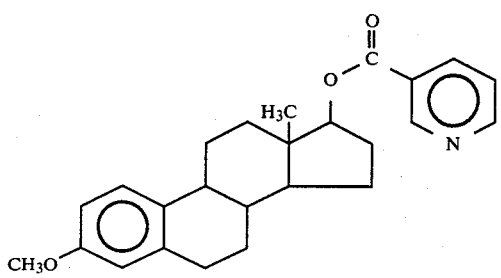

EXAMPLE 5

Preparation of 17β-[(1-Methyl-3-pyridinium)carbonyloxy]estra-1,3,5(10)-trien-3-ol 3-methyl ether iodide To 17β-nicotinoyloxyestra-1,3,5(10)-trien-3-ol 3-methyl ether (1.5 g, 0.0038 mol) in acetone (20 ml) was added methyl iodide (1 ml, 0.016 mol) and the mixture was refluxed overnight. The pale yellow precipitate was filtered, washed with acetone, and dried. Yield 76% (1.5595 g), m.p. 230°–234° C. (dec.). Anal. calculated for C$_{26}$H$_{32}$NO$_3$I: C, 58.53; H, 6.06; N, 2.63. Found: C, 58.25; H, 6.07; N, 2.59. The title compound has the formula:

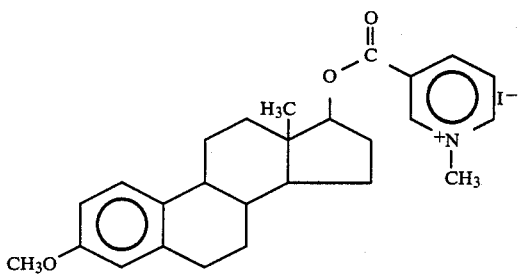

EXAMPLE 6

Preparation of 17β-[(1-Methyl-1,4-dihydro-3-pyridinyl)carbonyloxy]estra-1,3,5(10)-trien-3-ol 3-methyl ether To 17β-[(1-methyl-3-pyridinium)carbonyloxy]estra-1,3,5(10)-trien-3-ol 3-methyl ether (0.600 g, 1.12 mmol) in a 50:50 mixture of methanol and deaerated water (80 ml) were added NaHCO$_3$ (0.57 g, 6.7 mmol) and Na$_2$S$_2$O$_4$ (0.78 g, 4.5 mmol). The mixture was stirred under N$_2$ for 2 hours. The precipitate was filtered, dissolved in methanol at room temperature, filtered, and then reprecipitated with deaerated water. This precipitate was then filtered and dried over P$_2$O$_5$ under vacuum. Yield 74% (0.3383 g). The product decomposes over the range 120°–170° C. Anal. calculated for C$_{26}$H$_{33}$NO$_3$: C, 76.61; H, 8.18; N, 3.44. Found: C, 76.75; H, 8.43; N, 3.37. The product is further characterized by the structural formula:

(+1H₂O): C, 48.99; H, 4.89; N, 3.57. Found: C, 48.78; H, 4.66; N, 3.63. The product is further characterized by the structural formula:

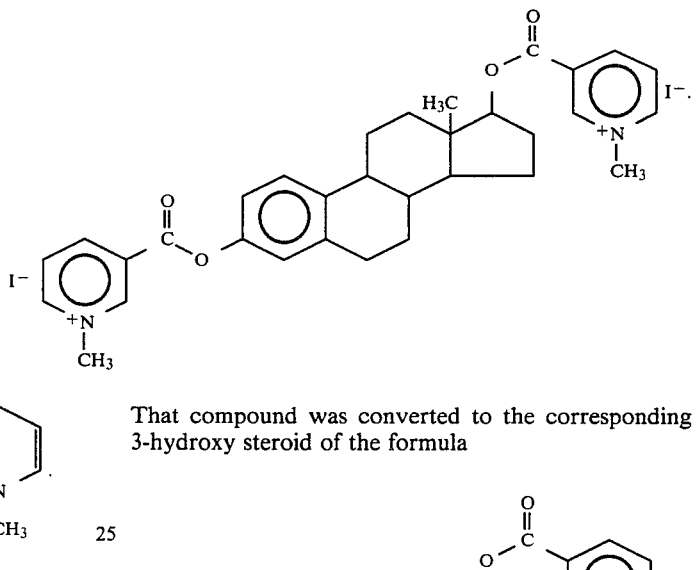

That compound was converted to the corresponding 3-hydroxy steroid of the formula

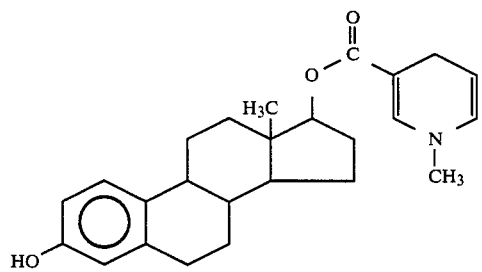

by partial hydrolysis; the resultant 3-hydroxy compound was then reduced, as generally described hereinabove, to afford the corresponding dihydro derivative of the formula

EXAMPLE 7

Preparation of Estra-1,3,5(10)-triene-3,17β-diol 3,17-dinicotinate (Estradiol 3,17β-dinicotinate)

Estradiol (2 g, 0.0073 mol) was added to nicotinoyl chloride hydrochloride (5.3 g, 0.029 mol) in dry pyridine (30 ml) at 0° C. The mixture was refluxed for 1 hour and then poured over 100 ml of ice water, filtered and dried over P₂O₅ under vacuum. Yield 90% (3.18 g), m.p. 148°–150° C. Anal. calculated for C₃₀H₃₁N₂O₄: C, 74.50; H, 6.47; N, 5.79. Found: C, 74.40; H, 6.32; N, 5.75. The product has the formula:

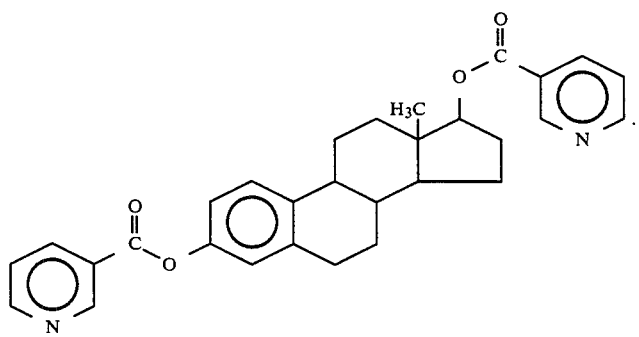

EXAMPLE 8

Preparation of 3,17β-Bis-[(1-methyl-3-pyridinium)carbonyloxy]estra-1,3,5(10)-triene diiodide Methyl iodide (1 ml, 0.016 mol) was added to estradiol 3,17β-dinicotinate (1 g, 0.0021 mol) in acetone (20 ml) and the mixture was refluxed overnight. The deep yellow precipitate which formed was filtered, washed with acetone, and dried. Yield 72% (1.262 g), m.p. 256°–258° C. (dec.). Anal. calculated for C₃₂H₃₆N₂O₄I₂

EXAMPLE 9

Preparation of Estra-1,3,5(10)-triene-3,17β-diol 17-nicotinate (Estradiol 17β-nicotinate)

0.5% Potassium bicarbonate in 95% methanol (60 ml) was added to estradiol 3,17β-dinicotinate (0.5 g, 0.0010 mol) and the slurry was stirred overnight at room temperature. Water (60 ml) was added and repeated extractions into chloroform were made, combined and dried over anhydrous sodium sulfate. The chloroform was removed in vacuo and the resulting pinkish-white solid was suspended in methanol at room temperature. The white powder thus obtained was separated by filtration and dried. Yield 94% (0.3663 g), m.p. 221°–222° C. Anal. calc. for $C_{24}H_{27}NO_3$: C, 76.36; H, 7.22; N, 3.71. Found: C, 76.20; H, 7.25; N, 3.70. The product has the formula:

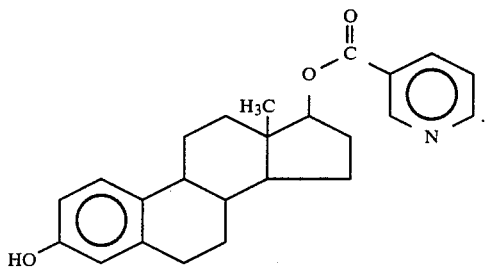

EXAMPLE 10

Preparation of 17β-[(1-Methyl-3-pyridinium)carbonyloxy]estra-1,3,5(10)-trien-3-ol iodide Methyl iodide (2 ml, 0.032 mol) was added to estra-1,3,5(10)-triene-3,17β-diol 17-nicotinate (2.0953 g, 0.0056 mol) in acetone (200 ml) and the mixture was refluxed overnight. The pale yellow precipitate which formed was removed by filtration, washed with acetone and dried. Yield 83% (2.4203 g), m.p. 268°–272° C. (dec.). Anal. calculated for $C_{25}H_{29}NO_3I$: C, 57.92; H, 5.65; N, 2.70. Found: C, 57.70; H, 5.73; N, 2.68. The product has the formula:

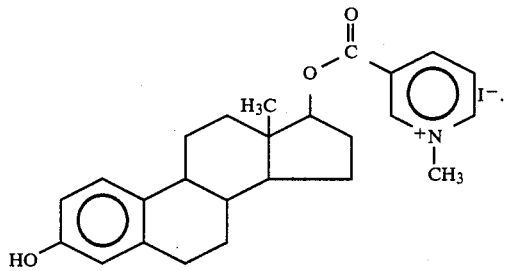

EXAMPLE 11

Preparation of 17β-[(1-Methyl-1,4-dihydro-3-pyridinyl)carbonyloxy]estra-1,3,5(10)-trien-3-ol To 17β-[(1-methyl-3-pyridinium)carbonyloxy]estra-1,3,5(10)-trien-3-ol iodide (1.09 g, 0.0021 mol) in 50:50 t-butanol/deaerated water (150 ml) was added NaHCO$_3$ (1.06 g, 0.0126 mol) and Na$_2$S$_2$O$_4$ (1.46 g, 0.0084 mol). The mixture was stirred under N$_2$ for one hour. The precipitate which formed was removed by filtration, dissolved in ether and dried over anhydrous Na$_2$SO$_4$. The ether was removed in vacuo. Yield 64% (0.2416 g). The product decomposes over the range 115°–130° C. Anal. calculated for $C_{25}H_{31}NO_3$ (+½H$_2$O): C, 74.59; H, 8.03; N, 3.48. Found: C, 74.57; H, 8.04; N, 3.40. The product is characterized by the structural formula:

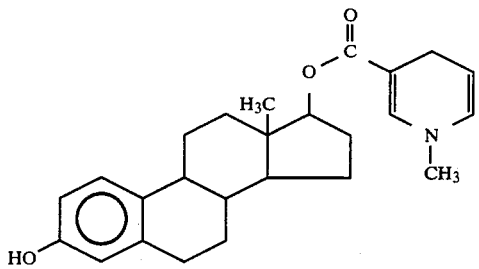

PHARMACOLOGICAL TESTING

The present invention is an outgrowth of animal testing designed to examine the dose-response and duration of estrogen-like activity following administration of a representative compound of formula (I), namely 17β-[(1-methyl-1,4-dihydro-3-pyridinyl)carbonyloxy]-estra-1,3,5(10)-trien-3-ol, hereafter referred to as CDS-E$_2$. We originally conducted this testing with a view toward use of the formula (I) compounds in reproductive medicine, e.g. for contraception and to treat gynecological disorders, as would be expected from the various Bodor applications and patents referred to hereinabove. Our testing showed surprisingly prolonged, severe suppression of LH levels in orchidectomized and ovariectomized rats as compared to estradiol itself, supporting the concept of use of the estrogen/carrier combinations for treatment of brain-specific, steroid deprivation syndromes (such as hot flushes) and for chronic reduction of gonadotropin secretion for fertility regulation or treatment of gonadal steroid-dependent diseases, such as endometriosis and prostatic hypertrophy. However, the studies were designed such that one of the parameters followed was body weight; this parameter was included simply as a means of verifying the central action of the drug. We observed a significant decrease in body weight gain in both orchidectomized and ovariectomized rats on day 12 post-treatment with CDS-E$_2$. This effect was maintained through day 24 and appeared to be dose-related. While equimolar doses of estradiol and estradiol benzoate also decreased body weight gain, their effect was smaller and more transient compared to the reductions induced by CDS-E$_2$. Results of representative experiments are set forth in Table I and Table II below. It can be seen from Table I that we have successfully identified a dose level of CDS-E$_2$, i.e. 0.1 mg/kg in ovariectomized rats, which dramatically reduces body weights without significantly affecting LH levels, uterine weights or anterior pituitary weights. These results suggest that, surprisingly, the effect on body weight can be separated from the effect on reproductive function in the case of the chemical delivery system used herein.

TABLE I

Response of Serum LH, Body Weight, Adenohypophysal Weight and Uterine Weight 12 Days Following Treatment with CDS-E$_2$ and Equimolar Estradiol in Ovariectomized Rats.

| Treatment Group (n) | LH (ng/mL) | Body Weight Gain (g) | Uterine Weight (mg) | Adenohypophyseal Weight (mg) | Days Cornified Epithelium |
|---|---|---|---|---|---|
| DMSO (9) 500 μL/kg | 5.91 ± 0.93[1,a] | 24.5 ± 1.7[a] | 196 ± 12[d] | 12.8 ± 0.6[d,e,f] | 0 |
| CDS-E$_2$ (10) 0.1 mg/kg | 4.04 ± 0.68[a,b] | 4.4 ± 2.7[b,c] | 241 ± 13[d] | 12.3 ± 0.6[e,f] | 3-7 |
| CDS-E$_2$ (6) 0.5 mg/kg | 4.48 ± 1.90[a,b] | −8.5 ± 3.2[d] | 334 ± 18[c] | 16.1 ± 0.6[c] | >10 |
| CDS-E$_2$ (4) 2.0 mg/kg | 1.45 ± 0.08[b] | −23.0 ± 3.4[d] | 489 ± 65[d] | 20.3 ± 0.6[b] | >11 |
| CDS-E$_2$ (5) 5.0 mg/kg | 0.51 ± 0.07[b] | −15.5 ± 2.2[d] | 647 ± 63[a] | 27.9 ± 0.9[a] | >11 |
| Estradiol (6) 0.07 mg/kg | 4.26 ± 1.01[a,b] | 27.3 ± 3.4[a] | 200 ± 12[d] | 12.6 ± 0.5[d,e,f] | 0 |
| Estradiol (4) 0.35 mg/kg | 3.87 ± 0.77[a,b] | 22.2 ± 4.3[a,b] | 187 ± 17[d] | 13.0 ± 0.4[c,d,e,f] | 0 |
| Estradiol (6) 1.38 mg/kg | 3.75 ± 0.36[a,b] | 14.5 ± 4.2[a,b] | 217 ± 16[d] | 13.9 ± 0.6[c,d,e] | 2-4 |
| Estradiol (6) 3.46 mg/kg | 3.66 ± 0.68[a,b] | −1.0 ± 6.0[c] | 210 ± 12[d] | 10.6 ± 0.5[f] | 3-5 |
| Estradiol (6) 10.38 mg/kg | 1.79 ± 0.70[b] | −13.3 ± 3.1[d] | 294 ± 27[c,d] | 15.4 ± 1.0[c,d] | 5-8 |

[1] mean ± SEM
[a-f] values with different superscripts are significantly different $p < 0.05$

TABLE II

Response of Serum LH, Body Weight and Adenohypophyseal Weight to Treatment of Orchidectomized Rats with CDS-E$_2$ and Equimolar Estradiol.

| Treatment Group (n) | Days Post Treatment | Serum LH (ng/mL) | Adenophyophyseal Weight (mg) | Body Weight Gain (g) |
|---|---|---|---|---|
| DMSO (7) 500 μL/kg | 12 | 6.83 ± 0.79[a] | 11.6 ± 0.6[a] | 56.3 ± 4.7 |
| CDS-E$_2$ (7) 3.0 mg/kg | 12 | 0.76 ± 0.38[b] | 15.5 ± 0.7[b] | 15.0 ± 5.1 |
| Estradiol (6) 2.1 mg/kg | 12 | 12.90 ± 1.65[c] | 13.0 ± 0.7[a] | 46.2 ± 4.1 |
| DMSO (7) 500 μL/kg | 18 | 12.42 ± 2.50[a] | 12.2 ± 0.6[a] | 53.6 ± 3.9 |
| CDS-E$_2$ (7) 3.0 mg/kg | 18 | 1.74 ± .70[a] | 16.2 ± 1.1[b] | −2.6 ± 4.6 |
| Estradiol (6) 2.1 mg/kg | 18 | 12.08 ± 0.91[a] | 12.8 ± 0.4[a] | 51.7 ± 8.3 |
| DMSO (7) 500 μL/kg | 24 | 8.58 ± 1.73[a] | 11.3 ± 0.5[a] | 73.3 ± 3.6 |
| CDS-E$_2$ (7) 3.0 mg/kg | 24 | 2.94 ± 1.10[b] | 14.0 ± 1.0[b] | 29.0 ± 6.0 |
| Estradiol (7) 2.1 mg/kg | 24 | 11.60 ± 1.35[a] | 13.3 ± 0.3[a,b] | 50.0 ± 6.7 |

[a-c] Values within a post-treatment time with different superscripts are significantly different $p < 0.05$.

Because of the surprisingly pronounced, prolonged and consistent effect on body weight observed with CDS-E$_2$, as compared to estradiol, it was of interest to investigate the effects on body weight in less estrogen-sensitive models. Therefore, the following study was designed to more closely characterize the effects of CDS-E$_2$ on weight gain in intact rats. Three doses of CDS-E$_2$ were compared to equimolar doses of estradiol and estradiol valerate in both sexes. Estradiol valerate was chosen for comparison purposes because it has been shown to yield prolonged estrogenic action in vivo and contains an ester group in the 17-position.

Young mature rats of the Sprague-Dawley strain (Charles Rivers Breeding Labs, Wilmington, MA) were housed 2 per cage in standard hanging wire mesh rat cages upon arrival in a climate controlled (22±2° C., lights on 0600-2000 hours) animal facility. Rats were provided with free access to Purina Rat Chow and tap water. After a 3 day acclimatization period, conscious restrained rats received a single injection via the tail vein of CDS-E$_2$, estradiol, estradiol valerate or dimethylsulfoxide vehicle (0.5 ml/kg). Each drug was administered at doses calculated as equimolar to 1.0, 5.0 and 15.0 mg/kg of CDS-E$_2$. Each of the 10 treatment groups initially contained 6 rats. Concurrent l treatment groups were performed in each sex. In order to better compare drug-induced changes in weight gain, rats were treated during the post-pubertal period of rapid weight gain (180-210 g). Vaginal epithelial cells were examined from daily vaginal lavages as an index of peripheral estrogenic activity. All rats were weighed at 3 day intervals during the initial 2 weeks and then at 16, 19 and 36 days post-treatment.

Figure 2:
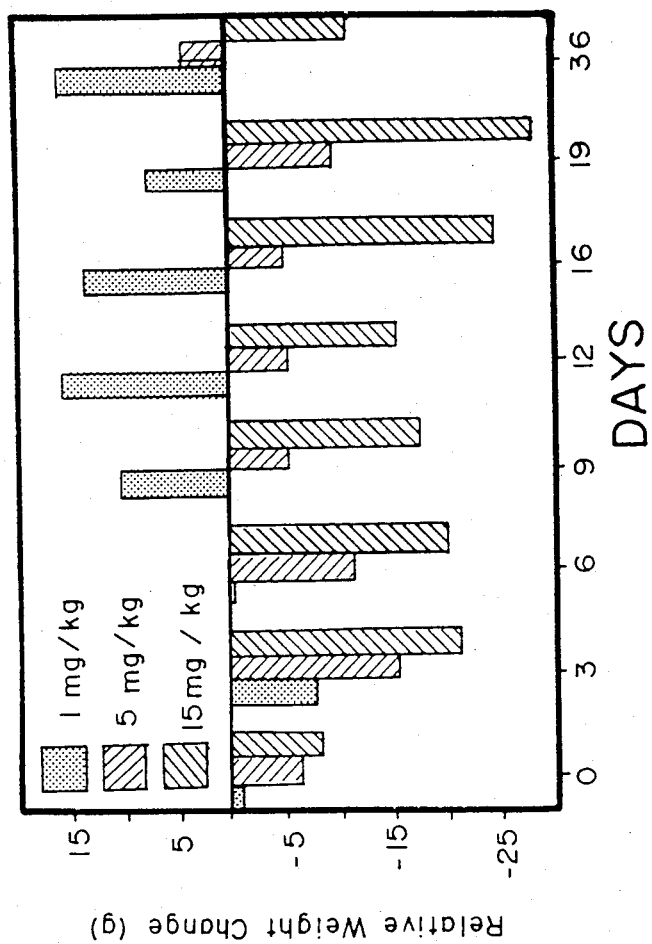
FIG. 2 is a bar graph illustrating the effects of 1 mg/kg ( ), 5 mg/kg ( ) and 15 mg/kg ( ) doses of a representative estradiol-CDS, i.e. 17 β-[(1-methyl-1,4-dihydro-3-pyridinyl)carbonyloxy]estra- 1,3,5(10)-trien-3-ol, on weight change relative to vehicle injected controls in intact female rats from 0 to 36 days post-treatment.

Data from each experiment were evaluated with the aid of a Lotus 1, 2, 3 software program (IBM). As expected, all animals progressively gained weight over the course of the experiment: however, the rate of weight gain was decreased in both males and females treated with CDS-E$_2$. See FIGS. 1 and 2, which depict the effects of CDS-E$_2$ on weight gain relative to vehicle injected controls in male (FIG. 1) and female (FIG. 2)

rats from 0 to 36 days post-treatment. Mean drug treatment group weight was subtracted from mean control weight for each day examined. FIGS. 1 and 2 illustrate that both the magnitude and duration of CDS-$E_2$ effect on weight gain is dose-related. Further, males appear to be more sensitive to this estrogenic effect on weight gain, as indicated from the near maximum response observed on days 6 through 19 post-treatment in the 5 mg/kg CDS-$E_2$ group (FIG. 1). As shown in FIG. 2, this 5 mg/kg dose clearly resulted in an intermediate response in females compared with lower and higher doses. Similarly, the lower dose mildly decreased weight gain in males until day 36, when weight gain appeared to increase compared to controls. This 10–15 g increase relative to controls was observed earlier (day 9) in females treated with 1 mg/kg CDS-$E_2$. Remarkably, a single 15 mg/kg dose of CDS-$E_2$ decreased body weight gain in both males and females for the entire 36 day duration of the study. Both the vigorous appearance of treated animals and the return toward control weight values indicate that the effects of this drug are unlikely due to toxicity and are reversible. Moreover, even at the lower dosage level of 5 mg/kg, significant decreases in body weight gain in both sexes were observed for CDS-$E_2$, although the decreases were not as pronounced and the duration of activity was not as long as that seen at the 15 mg/kg level. Furthermore, from daily examination of vaginal epithelial cells, it appeared that female rats, even at the highest CDS-$E_2$ dose level of 15 mg/kg, continued to cycle, albeit the cycles exhibited a longer and/or more irregular pattern such as is normally seen in older (i.e. middle-aged) females. These results suggest that a dosge could be selected between about 1 and 5 mg/kg which would lower weight gain in female rats while having an even less significant effect on the estrous cycle. Since male rats appear to be even more sensitive to the effects of CDS-$E_2$ on weight gain, such a lower dose would also be expected to lower weight gain in males.

Figure 3:
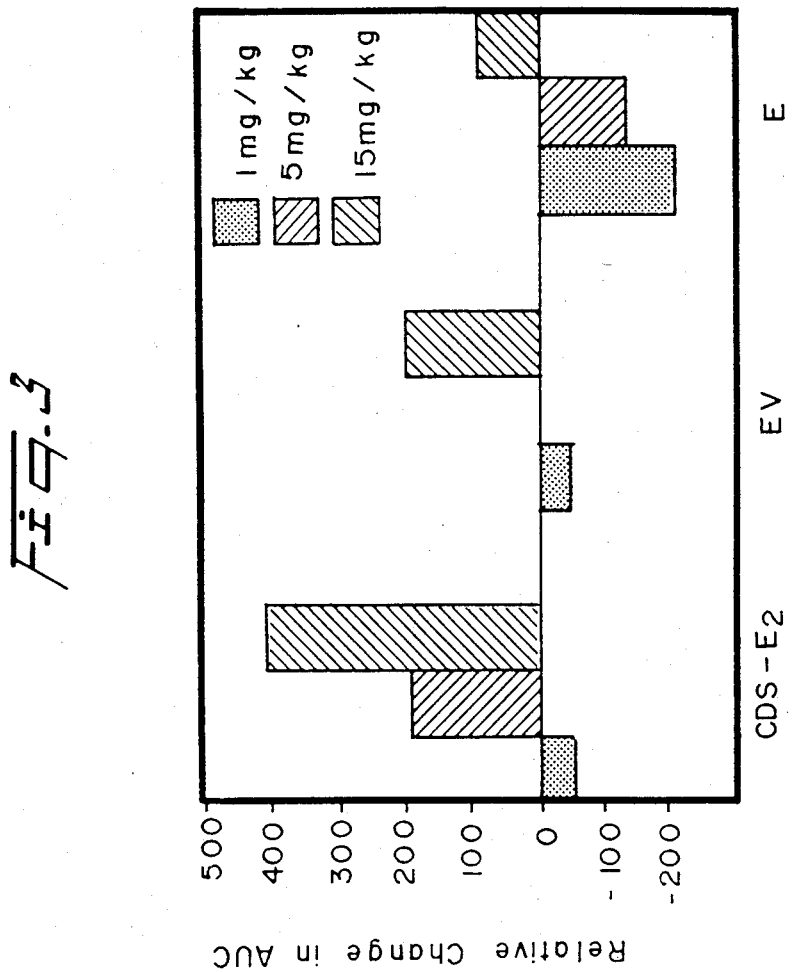
FIG. 3 is a bar graph illustrating the dose response effects of 1 mg/kg ( ), 5 mg/kg ( ) and 15 mg/kg ( ) doses of a representative estradiol]-CDS, i.e. 17 β-[(1-methyl-1,4-dihydro-3-pyridinyl)carbonyloxy]estra-1,3,5(10)-trien-3-ol (CDS-E$_2$), and of equimolar doses of estradiol valerate (EV) and estradiol (E) on the magnitude of cumulative weight loss through day 19 post-treatment in intact male rats.
Figure 4:
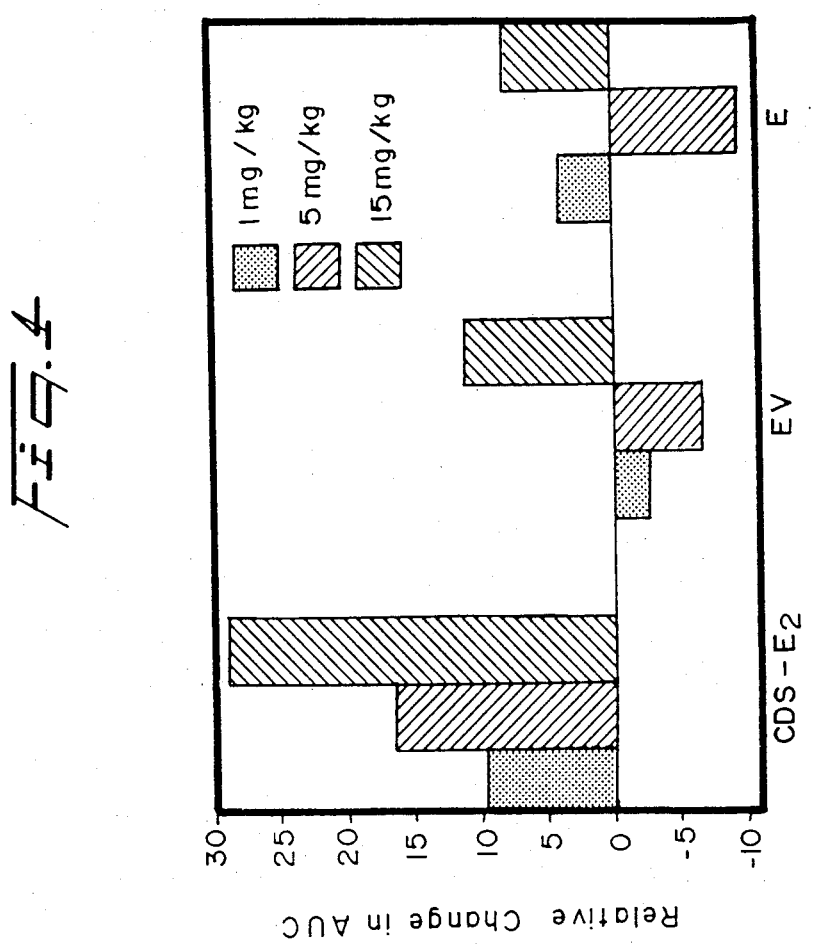
FIG. 4 is a bar graph illustrating the dose response effects of 1 mg/kg ( ), 5 mg/kg ( ) and 15 mg/kg ( ) doses of a representative estradiol-CDS, i.e. 17 β-[(1-methyl-1,4-dihydro-3-pyridinyl)carbonyloxy]estra-1,3,5(10)-trien-3-ol (CDS-E$_2$), and of equimolar doses of estradiol valerate (EV) and estradiol (E) on the magnitude of cumulative weight loss through day 6 post-treatment in intact female rats.

The effects of CDS-$E_2$ on body weight in comparison to two other widely used estrogenic compounds in the experiment described above are better shown in FIGS. 3 and 4. These figures illustrate the cumulative effects of equimolar doses of estradiol and estradiol valerate compared to CDS-$E_2$. FIG. 3 shows the dose response effects of CDS-$E_2$, estradiol and estradiol valerate on the magnitude of cumulative weight loss through day 19 post-treatment in male rats. Individual weight gains were calculated and averaged for each day and treatment group and then expressed as percent change from initial weight (day 0). Area under the curve (AUC) of percent weight change vs. time was estimated by the trapezoidal method for each of the 10 treatment groups. Area under the curve for each of the 9 drug treatment groups are subtracted from area under the DMSO control curve as an index of cumulative weight loss. FIG. 4 shows the dose response effects of CDS-$E_2$, estradiol and estradiol valerate on the magnitude of weight loss through day 6 post-treatment in female rats. Calculations of individual weight gains and AUC's were done in the same manner as for FIG. 3.

The progressive reduction in body weight relative to control with increasing doses of CDS-$E_2$ is clearly evident in FIG. 3 (males) and FIG. 4 (females). This response is consistent with a sustained central estrogenic action of CDS-$E_2$. Further, a predicted order of potency was observed in the degree of weight loss index found after the high doses of CDS-$E_2$, estradiol valerate and estradiol in both males and females.

These data strongly indicate that a representative compound of formula (I), CDS-$E_2$, can be used as an effective aid to control body weight. Evidence thus far has shown no deleterious side-effects and the primary effect appears to be reversible. In as much as the dose of estradiol valerate equimolar to 15 mg/kg of CDS-$E_2$ was immediately lethal for 4 of 6 rats treated, while all rats treated with CDS-$E_2$ thrived for the 36 day duration of the study, this form of CNS estradiol delivery appears to have a wider therapeutic index than a sustained release estrogen formulation such as the valerate ester.

Compositions for use in the method of this invention comprise an effective weight-controlling amount of a compound of formula (I) above or a non-toxic pharmaceutically acceptable salt thereof, and a non-toxic pharmaceutically acceptable carrier therefor.

Suitable non-toxic pharmaceutically acceptable carriers for use with the selected compound of formula (I), e.g. those less toxic than the target drug species themselves, will be apparent to those skilled in the art of pharmaceutical formulation. See, for example, *Remington's Pharmaceutical Sciences*, seventeenth edition, ed. Alfonso R. Gennaro, Mack Publishing Company, Easton, Pa. (1985). Obviously, the choice of suitable carriers will depend upon the exact nature of the particular dosage form selected, as well as upon the identity of the compound to be administered. The therapeutic dosage range for administration of a compound of formula (I) for use in weight control can be estimated on the basis of animal test results detailed hereinabove. Naturally, such therapeutic dosage ranges will vary with the particular compound of formula (I) used, the size, species and condition of the subject, the severity of the subject's weight problem, the particular dosage form employed, the route of administration and the like. And and quantity of given dosage form needed to deliver the desired dose will of course depend upon the concentration of the compound of formula (I) in any given pharmaceutical composition/dosage form thereof.

The compounds of formula (I) exhibit very long-acting effects on weight control; however, the length of action appears to be dose-related. Moreover, the dose level also appears to determine the extent of direct effects on the female reproductive cycle. Judicious selection of dose level therefore should be used. Lower doses, administered more frequently, may be desirable in cases where effects on the reproductive cycle should be minimized. Moreover, it is believed that a substantial lowering effect on weight can be achieved in females by administering the formula (I) compound so that it acts during only part of the reproductive cycle, i.e., so that the compound exerts its weight-controlling effect primarily during the luteal phase, the portion of the cycle in which endogenous estrogen activity is lower. Such administration would also serve to minimize effects on the reproductive cycle; in humans, endogenous estrogen influence declines after ovulation and is at its lowest during the few days which precede menstruation, so that administration during the second half of the menstrual cycle would maximize the weight control effect while minimizing the effect on the reproductive cycle. The dosage level would be accordingly adjusted downward, so that the compound administered would not continue to exert substantial effects during the first half of the subsequent cycle.

When it is not important that cycling be maintained, the compounds of formula (I) may be used at the higher, longer-acting levels. Moreover, the active ingredient may be formulated into a substained release carrier system and/or a route of administration may be selected to slowly release the chemical, e.g. subcutaneous implantation.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What we claim is:

1. A method for mammalian weight control, said method comprising administering to a mammal in need of such treatment, an amount effective to reduce or maintain said mammal's weight of a compound of the formula

[E—DHC]   (I)

or a non-toxic pharmaceutically acceptable salt thereof, wherein [E] is an estrogen and [DHC] is the reduced, biooxidizable, blood-brain barrier penetrating, lipoidal form of a dihydropyridine⇌pyridinium salt redox carrier.

2. A method according to claim 1, said method comprising administering to a mammal in need of such treatment, an amount effective to reduce or maintain said mammal's weight of a compound of the formula E[DHC]$_n$   (Ia)

or a non-toxic pharmaceutically acceptable salt thereof, wherein E— is the residue of an estrogen containing at least one reactive hydroxyl functional group, said residue being characterized by the absence of a hydrogen atom from at least one of said reactive functional groups in said estrogen; n is a positive integer equal to the number of said functional groups from which a hydrogen atom is absent; and [DHC] is the reduced, biooxidizable, blood-brain barrier penetrating, lipoidal form of a dihydropyridine⇌pyridinium salt redox carrier.

3. A method according to claim 2, wherein n is 1 or 2.

4. A method according to claim 2, wherein E— is the residue of a natural or semisynthetic estrogen.

5. A method according to claim 2, wherein E— is the residue of a 3-monohydroxy, 17-monohydroxy or 3,17-dihydroxy steroid having an aromatic A-ring.

6. A method according to claim 2, wherein E— is a residue of estradiol.

7. A method according to claim 2, wherein E— is the residue of a 3- or 17-monoester of estradiol.

8. A method according to claim 2, wherein E— is the residue of estradiol benzoate, estradiol cypionate, estradiol enanthate, estradiol undecylate, estradiol valerate, estradiol propionate or estradiol undecenylate.

9. A method according to claim 2, wherein E— is the residue of estrone.

10. A method according to claim 2, wherein E— is a residue of estriol.

11. A method according to claim 2, wherein E— is a residue of ethinyl estradiol.

12. A method according to claim 2, wherein E— is the residue of mestranol.

13. A method according to claim 2, wherein E— is the residue of quinestrol, estrazinol or estrofurate or a residue of nylestriol.

14. A method according to claim 2, wherein [DHC] is 4,617,298

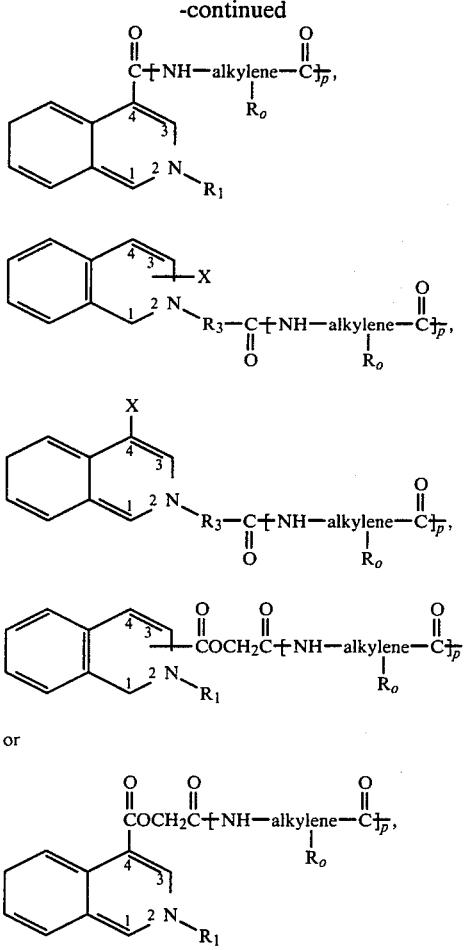

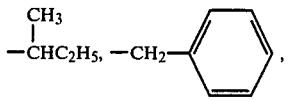

—(CH₂)₂—SCH₃,  —CH₂—CONH₂ or  —CH₂CH₂—CONH₂.

18. A method according to claim 14, wherein R₁ is —CH₃.

19. A method according to claim 14, wherein R₃ is —CH₂CH₂—.

20. A method according to claim 14, wherein X is —CONH₂.

21. A method according to claim 14, wherein the depicted carbonyl-containing groupings in formulas (a') and (c') and the X substituent in formula (b') are attached at the 3-position of the dihydropyridine ring; the depicted carbonyl-containing groupings in formulas (d') and (f') and the X substituent in formula (e') are attached at the 3-position of the dihydroquinoline ring; and the depicted carbonyl-containing groupings in formulas (g') and (j') and the X substituent in formula (h') are attached at the 4-position of the dihydroisoquinoline ring.

22. A method according to claim 14, wherein [DHC] is

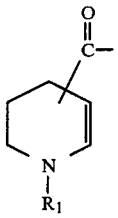

wherein R₁ is C₁-C₇ alkyl, C₁-C₇ haloalkyl or C₇-C₁₀ aralkyl, the dotted line indicates the presence of a double bond in either the 4 or 5 position of the dihydropyridine ring and the carbonyl group can be attached at the 2, 3 or 4 position of the dihydropyridine ring.

23. A method according to claim 22, wherein [DHC] is

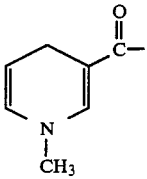

24. A method according to claim 23, wherein E— is a residue of estradiol.

25. A method according to claim 2, wherein the compound of formula (Ia) is 17β-[(1-methyl-1,4-dihydro-3-pyridinyl)carbonyloxy]estra-1,3,5(10)-trien-3-ol.

26. A method according to claim 1, said method comprising administering to a mammal in need of such treatment, an amount of a compound of the formula

[E—DHC]                                    (I)

or a non-toxic pharmaceutically acceptable salt thereof, wherein [E] is an estrogen and [DHC] is the reduced, biooxidizable, blood-brain barrier penetrating, lipoidal

--- wherein the alkylene group can be straight or branched and can contain 1 to 3 carbon atoms; R₀ is a radical identical to the corresponding portion of a natural amino acid; p is 0, 1 or 2, provided that, when p is 2, then the alkylene groups can be the same or different and the R₀ radical can be the same or different; the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihydroquinoline ring; R₁ is C₁-C₇ alkyl, C₁-C₇ haloalkyl or C₇-C₁₀ aralkyl; R₃ is C₁-C₃ alkylene; X is —CONR'R" wherein R' and R", which can be the same or different, are each H or C₁-C₇ alkyl, or X is —CH=NOR''' wherein R''' is H or C₁-C₇ alkyl; the carbonyl-containing groupings in formulas (a') and (c') and the X substituent in formula (b') can each be attached at the 2, 3 or 4 position of the dihydropyridine ring; the carbonyl-containing groupings in formulas (d') and (f') and the X substituent in formula (e') can each be attached at the 2, 3 or 4 position of the dihydroquinoline ring; and the carbonyl-containing groupings in formulas (g') and (j') and the X substituent in formula (h') can each be attached at the 1, 3 or 4 position of the dihydroisoquinoline ring.

15. A method according to claim 14, wherein p is 0.

16. A method according to claim 14, wherein p is 1.

17. A method according to claim 14, wherein p is 1 or 2, alkylene is —CH₂— and R₀ is H, —CH₃—, —CH(CH₃)₂, —CH₂—CH(CH₃)₂, form of a dihydropyridine⇌pyridinium salt redox carrier, said amount being sufficient to cause a lowering effect on body weight but insufficient to cause cessation of the estrous or menstrual cycle in the female of the species.

27. A method according to claim 26, wherein said compound is administered to a female mammal only during the luteal phase of the female's estrous or menstrual cycle.

* * * * *

UNITED STATES PATENT AND TRADEMARK OFFICE
CERTIFICATE OF CORRECTION

PATENT NO. : 4,617,298
DATED : October 14, 1986
INVENTOR(S) : NICHOLAS S. BODOR; KERRY S. ESTES; JAMES W. SIMPKINS It is certified that error appears in the above-identified patent and that said Letters Patent is hereby corrected as shown below:

| | |
|---|---|
| column 2, line 56: | "Morten" should read --Morton--. |
| column 2, line 56: | "Am. j." should read --Am. J.--. |
| column 4, lines 58-59 and 65-66; and column 5, lines 5-6 and 13-14: | "1 mg/kg (　), 5 mg/kg (　) and 15 mg/kg (　)" should read, at each occurence, --1 mg/kg (), 5 mg/kg () and 15 mg/kg ()--. |
| column 5, line 6: | "estradiol]" should read --estradiol--. |
| column 5, line 51: | "Cs/áky" should read --Csáky--. |
| column 5, line 58: | "E[DHC]$_n$" should read --E$-$[DHC]$_n$--. |

UNITED STATES PATENT AND TRADEMARK OFFICE
CERTIFICATE OF CORRECTION

PATENT NO. : 4,617,298

DATED : October 14, 1986

INVENTOR(S) : NICHOLAS S. BODOR; KERRY S. ESTES; JAMES W. SIMPKINS

It is certified that error appears in the above-identified patent and that said Letters Patent is hereby corrected as shown below:

column 6, line 6: "17 monesters" should read --17 monoesters--.

column 6, line 55: "[E—DHC].HX" should read --[E—DHC]·HX--.

column 7, line 19: "E[QC$^+$]$_n$qX$^{-t}$" should read --E—[QC$^+$]$_n$qX$^{-t}$--.

column 10, in structures (a'), (b') and (c'), at each occurrence:

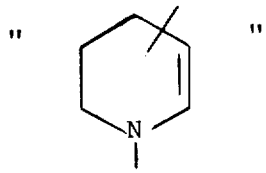 should read 

column 10, in structures (d') and (e') and column 11, in structure (f'), at each occurrence:

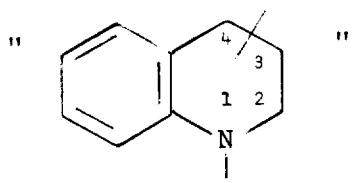 should read 

UNITED STATES PATENT AND TRADEMARK OFFICE
CERTIFICATE OF CORRECTION

PATENT NO. : 4,617,298

DATED : October 14, 1986

INVENTOR(S) : NICHOLAS S. BODOR; KERRY S. ESTES; JAMES W. SIMPKINS

It is certified that error appears in the above-identified patent and that said Letters Patent is hereby corrected as shown below:

column 15, in the structures for mestranol and its quaternary intermediate (cation) and dihydro derivative, at each occurrence:

" 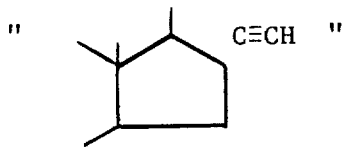 "   should read   -- 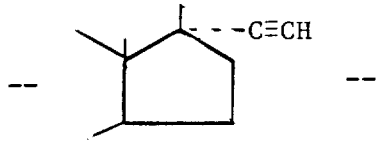 -- columns 15 and 16, add the following structures from page 28 of the application:

| STARTING MATERIAL | QUATERNARY INTERMEDIATE(CATION) | DIHYDRO DERIVATIVE |

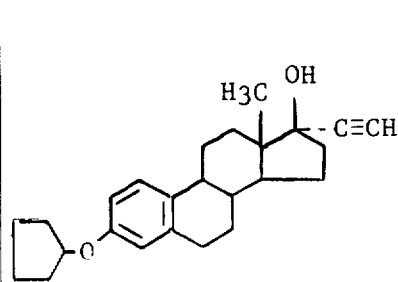 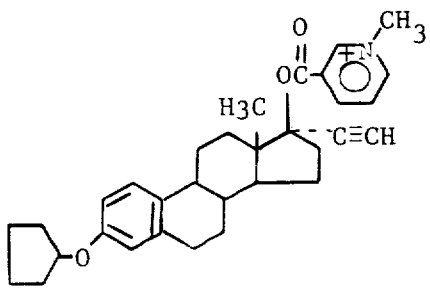 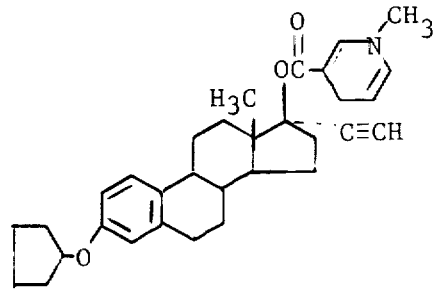

Quinestrol

UNITED STATES PATENT AND TRADEMARK OFFICE
CERTIFICATE OF CORRECTION

PATENT NO. : 4,617,298  Page 4 of 10
DATED : October 14, 1986
INVENTOR(S) : NICHOLAS S. BODOR; KERRY S. ESTES; JAMES W. SIMPKINS It is certified that error appears in the above-identified patent and that said Letters Patent is hereby corrected as shown below:

columns 15 and 16, add the following structures from page 28 of the application:

| STARTING MATERIAL | QUATERNARY INTERMEDIATE(CATION) | DIHYDRO DERIVATIVE |

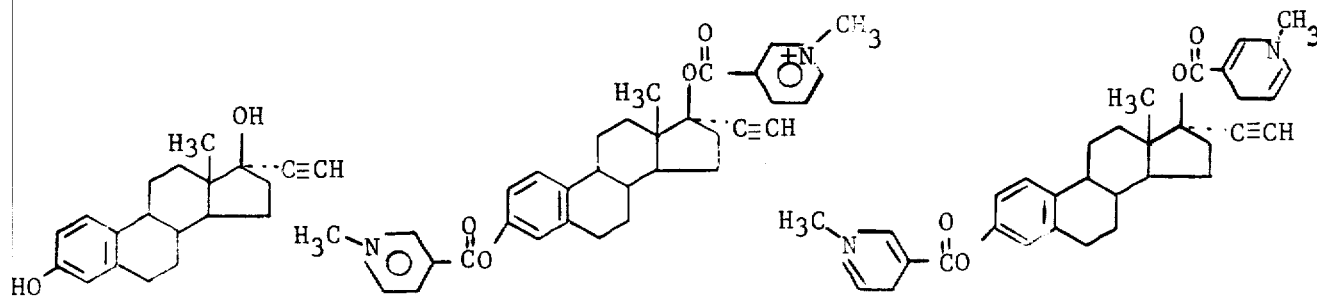

Ethinyl estradiol

UNITED STATES PATENT AND TRADEMARK OFFICE
CERTIFICATE OF CORRECTION

PATENT NO. : 4,617,298

DATED : October 14, 1986

INVENTOR(S) : NICHOLAS S. BODOR; KERRY S. ESTES; JAMES W. SIMPKINS

It is certified that error appears in the above-identified patent and that said Letters Patent is hereby corrected as shown below:

columns 17 and 18, in the structures for ethinyl estradiol and its quaternary intermediate (cation) and dihydro derivative, at each occurrence:

" 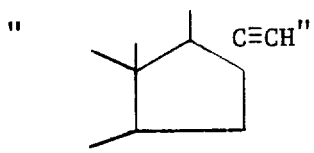 "     should read     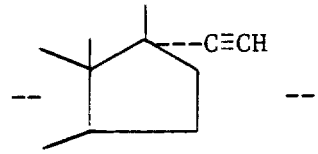

columns 19-20, in the structures for mestranol and its quaternary intermediate (cation) and dihydro derivative, at each occurrence:

" 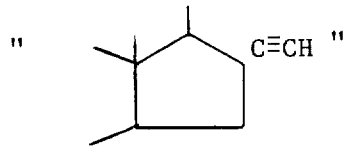 "     should read __ 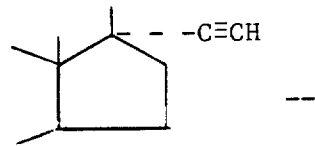 __ column 20, line 33:     "prepared from" should read --(prepared from--.

UNITED STATES PATENT AND TRADEMARK OFFICE
CERTIFICATE OF CORRECTION

PATENT NO. : 4,617,298

DATED : October 14, 1986

INVENTOR(S) : NICHOLAS S. BODOR; KERRY S. ESTES; JAMES W. SIMPKINS

It is certified that error appears in the above-identified patent and that said Letters Patent is hereby corrected as shown below:

columns 23-24, in the structures for mestranol and its quaternary intermediate (cation) and dihydro derivative, at each occurrence:

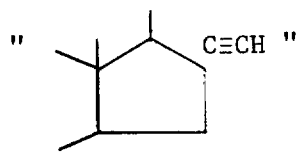   should read   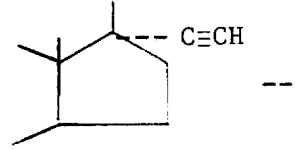

columns 25-26:  the sentence in fine print below the structures should be appended to the structure for estradiol's quaternary intermediate (cation).

column 28, line 23:  the comma after "procedures" should be deleted.

columns 29-31:  the sentence in fine print below the structures in column 31 should be appended to the structures for estradiol's quaternary intermediate (cation) in column 29.

UNITED STATES PATENT AND TRADEMARK OFFICE
CERTIFICATE OF CORRECTION

PATENT NO. : 4,617,298

DATED : October 14, 1986

INVENTOR(S) : NICHOLAS S. BODOR; KERRY S. ESTES; JAMES W. SIMPKINS

It is certified that error appears in the above-identified patent and that said Letters Patent is hereby corrected as shown below:

column 30, in the structures for ethinyl estradiol and mestranol and their quaternary intermediates (cations) and their dihydro derivatives, at each occurrence:

" 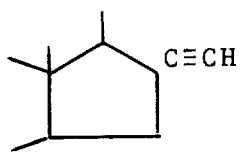 "  should read  -- 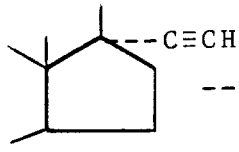 -- column 31, in the structures for quinestrol and its quaternary intermediate (cation) and dihydro derivative, at each occurrence:

" 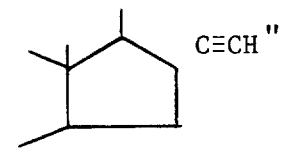 "  should read  -- 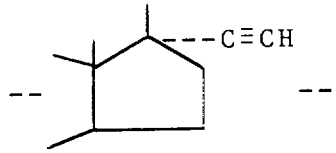 --

UNITED STATES PATENT AND TRADEMARK OFFICE
CERTIFICATE OF CORRECTION

PATENT NO. : 4,617,298

DATED : October 14, 1986

INVENTOR(S) : NICHOLAS S. BODOR; KERRY S. ESTES; JAMES W. SIMPKINS

It is certified that error appears in the above-identified patent and that said Letters Patent is hereby corrected as shown below:

columns 33-34, in the structures for mestranol and its quaternary intermediate (cation) and dihydro derivative, at each occurrence:

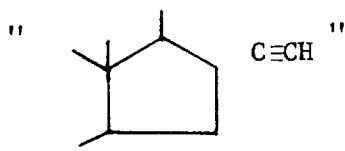  should read  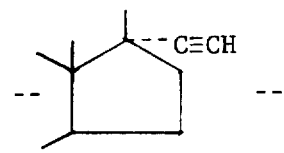

columns 37-38, in the two structures for mestranol and in the structures for its quaternary intermediate (cation) and dihydro derivative, at each occurrence:

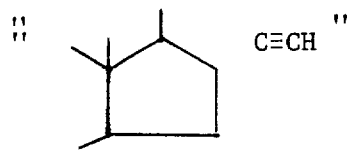  should read  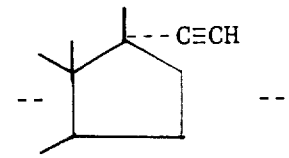

column 37, line 40:  "METHOD D" should read --METHOD J--.

UNITED STATES PATENT AND TRADEMARK OFFICE
CERTIFICATE OF CORRECTION

PATENT NO. : 4,617,298

DATED : October 14, 1986

INVENTOR(S) : NICHOLAS S. BODOR; KERRY S. ESTES; JAMES W. SIMPKINS

It is certified that error appears in the above-identified patent and that said Letters Patent is hereby corrected as shown below:

column 48, line 52: "Concurrent 1 treatment" should read --Concurrent studies with identical treatment--.

column 49, line 33: "dosge" should read --dosage--.

column 50, line 38: "And and" should read --And the--.

column 51, line 35: "E[DHC]$_n$" should read --E ─[DHC]$_n$--.

column 52, in structures (a'), (b') and (c'), at each occurrence:

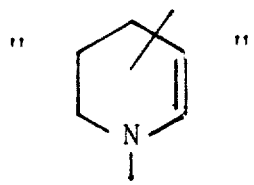   should read   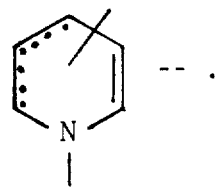   .

Column 52, in structures (d'), (e') and (f'), at each occurrence:

UNITED STATES PATENT AND TRADEMARK OFFICE
CERTIFICATE OF CORRECTION

PATENT NO. : 4,617,298

DATED : October 14, 1986

INVENTOR(S) : Nicholas S. Bodor; Kerry S. Estes; James W. Simpkins

It is certified that error appears in the above-identified patent and that said Letters Patent is hereby corrected as shown below:

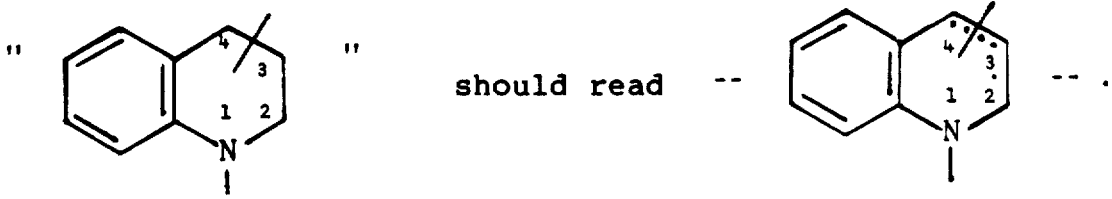

column 53, line 44: "radical" should read --radicals--.

column 53, line 67: "-CH₃-" should read -- -CH₃ -- column 54, line 35, in the structure:

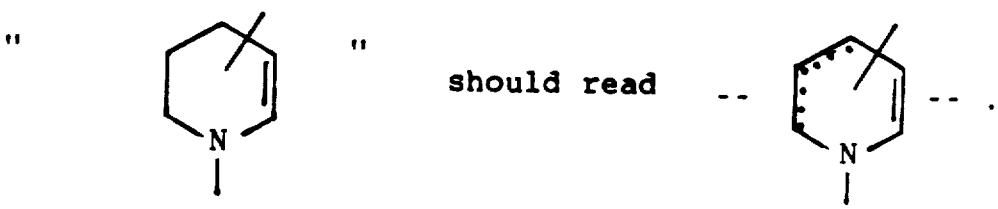

Signed and Sealed this

Twenty-fifth Day of August, 1987

Attest:

DONALD J. QUIGG

Attesting Officer    Commissioner of Patents and Trademarks